(12) United States Patent
Hoque et al.

(10) Patent No.: US 12,427,506 B1
(45) Date of Patent: Sep. 30, 2025

(54) METHOD FOR CARBON DIOXIDE FIXATION USING A PALLADIUM-DOPED NITROGEN-RICH ORGANIC FRAMEWORK CATALYST

(71) Applicant: King Fahd University of Petroleum and Minerals, Dhahran (SA)

(72) Inventors: Bosirul Hoque, Dhahran (SA); Aasif Helal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 19/210,905

(22) Filed: May 16, 2025

(51) Int. Cl.
| | |
|---|---|
| *B01J 31/16* | (2006.01) |
| *B01J 31/02* | (2006.01) |
| *B01J 31/40* | (2006.01) |
| *B01J 35/30* | (2024.01) |
| *B01J 35/40* | (2024.01) |
| *B01J 35/51* | (2024.01) |
| *B01J 35/64* | (2024.01) |
| *B01J 37/00* | (2006.01) |

(Continued)

(52) U.S. Cl.
CPC ....... *B01J 31/1691* (2013.01); *B01J 31/0239* (2013.01); *B01J 31/4038* (2013.01); *B01J 35/393* (2024.01); *B01J 35/40* (2024.01); *B01J 35/51* (2024.01); *B01J 35/643* (2024.01); *B01J 37/009* (2013.01); *B01J 37/04* (2013.01); *B01J 37/06* (2013.01); *B01J 37/16* (2013.01); *B01J 38/02* (2013.01); *B01J 38/48* (2013.01); *C07D 317/36* (2013.01); *B01J 2231/4288* (2013.01); *B01J 2531/824* (2013.01)

(58) Field of Classification Search
CPC ............ B01J 31/1691; B01J 31/0239; B01J 31/4038; B01J 35/393; B01J 35/40; B01J 35/51; B01J 35/643; B01J 37/009; B01J 37/04; B01J 37/06; B01J 37/16; B01J 38/02; B01J 38/48; B01J 2231/4288; B01J 2531/824; C07D 317/36
USPC ........................................................ 549/229
See application file for complete search history.

(56) References Cited

FOREIGN PATENT DOCUMENTS

| | | |
|---|---|---|
| CN | 108355719 B | 8/2020 |
| CN | 116731225 A | 9/2023 |
| CN | 118558364 A | 8/2024 |

OTHER PUBLICATIONS

Srinivasappa et al, Synthesis of Vinylene-Linked Covalent Organic Frameworks from Acetonitrile: Combining Cyclotrimerization and Aldol Condensation , ACS Sustainable Chem. Eng. 2024, 12, 9428-9445. (Year: 2024).*

(Continued)

*Primary Examiner* — Taylor V Oh
(74) *Attorney, Agent, or Firm* — Oblon, McClelland, Maier & Neustadt, L.L.P.

(57) ABSTRACT

A method of carbon dioxide fixation includes contacting a covalent organic framework material with a co-catalyst and an epoxide in the presence of carbon dioxide to form a cyclic carbonate. The covalent organic framework material includes reacted units of a 2,4,6-trimethyl-1,3,5-triazine, reacted units of a 4,4'-biphenyldicarbaldehyde, and palladium nanoparticles. The reacted units of the 2,4,6-trimethyl-1,3,5-triazine and the reacted units of the 4,4'-biphenyldicarbaldehyde form a COF-701, where the palladium nanoparticles are on an outer surface of the COF-701. The co-catalyst is n-tetrabutylammonium bromide.

19 Claims, 33 Drawing Sheets

(51) Int. Cl.
  *B01J 37/04* (2006.01)
  *B01J 37/06* (2006.01)
  *B01J 37/16* (2006.01)
  *B01J 38/02* (2006.01)
  *B01J 38/48* (2006.01)
  *C07D 317/36* (2006.01)

(56) References Cited

OTHER PUBLICATIONS

Acharjya et al ,Harnessing the Engineered 2D Triazine-Based Metal-Anchored Covalent-Organic Framework as a Catalyst for Selective Conversion of CO2 into Value-Added Products at Atmospheric Pressure, J. Am. Chem. Soc. 2020, 142, 14033-14038 (Year: 2020).*
Wikipedia ,Palladium, Aug. 2024, p. 1-14. (Year: 2024).*
Hao Lyu, et al., "Porous Crystalline Olefin-Linked Covalent Organic Frameworks", Journal of the American Chemical Society, vol. 141, Apr. 19, 2019, pp. 6848-6852.
Jérôme Roeser, et al., "Covalent Triazine Frameworks as Heterogeneous Catalysts for the Synthesis of Cyclic and Linear Carbonates from Carbon Dioxide and Epoxides", ChemSusChem, vol. 5, Aug. 16, 2012, pp. 1793-1799.

* cited by examiner

METHOD FOR CARBON DIOXIDE FIXATION USING A PALLADIUM-DOPED NITROGEN-RICH ORGANIC FRAMEWORK CATALYST

BACKGROUND

Technical Field

The present disclosure relates to chemical catalysis and carbon dioxide utilization, and more particularly, pertains to a method for fixing carbon dioxide into cyclic carbonates using a covalent organic framework material.

Description of Related Art

The "background" description provided herein is for the purpose of generally presenting the context of the disclosure. The work of the presently named inventors, to the extent it is described in this background section, as well as aspects of the description which may not otherwise qualify as prior art at the time of filing, are neither expressly nor impliedly admitted as prior art against the present disclosure.

Escalating levels of atmospheric carbon dioxide ($CO_2$) due to rapid industrialization and urbanization present a challenge to global environmental stability and sustainable development. Modem infrastructure, transportation, and energy generation are among leading contributors to greenhouse gas emissions, collectively accounting for about 80% of total $CO_2$ output worldwide. Reversing modernization is not a viable mitigation strategy. Focus must shift toward integrated solutions that incorporate carbon capture, utilization, and storage (CCUS) to manage environmental consequences of anthropogenic $CO_2$ emissions [Crittenden, J. C. and White. H. S., Harnessing energy for a sustainable world, *J Am Chem Soc*, 2010, 132, 13, 4503-4505].

Conversion of $CO_2$ into industrially relevant value-added products has garnered attention as a complementary strategy to sequestration [Kosaka, F. et al., Enhanced activity of integrated $CO_2$ capture and reduction to $CH_4$ under pressurized conditions toward atmospheric $CO_2$ utilization, *ACS Sustain Chem Eng*, 2021, 9, 9, 3452-3463]. Although $CO_2$ has been employed for decades in the manufacture of urea, salicylic acid, fire extinguishers, and refrigerants, such applications constitute less than 1% of total $CO_2$ emissions, underscoring the need for expanded utilization avenues [North, M. et al., Synthesis of cyclic carbonates from epoxides and $CO_2$, *Green chemistry*, 2010, 12, 9, 1514]. One route for expanded utilization is synthesis of cyclic carbonates, which are compounds that serve as aprotic solvents, battery electrolytes, polymer monomers, and chemical intermediates, through catalytic fixation of $CO_2$ with epoxides [Fukuoka, S. et al., A novel non-phosgene polycarbonate production process using by-product CO2 as starting material, *Green Chem*, 2003, 5, 5, 497-507; and Clements, J. H., Reactive applications of cyclic alkylene carbonates, *Ind Eng Chem Res*, 2003, 42, 4, 663-674].

Conventional synthesis of cyclic carbonates typically proceeds by coupling $CO_2$ with strained epoxides in the presence of catalytic systems [Hu, Y., et al., Polyethers as complexing agents in calcium-catalyzed cyclic carbonate synthesis, *ACS Sustain Chem Eng*, 2019, 7, 15, 13257-13269]. Industrial-scale implementation of this reaction has been historically achieved using quaternary ammonium salts at elevated pressures and temperatures [Pescarmona, P. P., Cyclic carbonates synthesised from $CO_2$: Applications, challenges and recent research trends, *Curr Opin Green Sustain Chem*, 2021, 29, 100457]. To align this process with principles of green chemistry and energy efficiency, recent efforts have focused on developing catalysts capable of operating under milder, ambient conditions [Sengupta, M. et al., CuxOy@COF: An efficient heterogeneous catalyst system for $CO_2$ cycloadditions under ambient conditions, *Journal of $CO_2$ Utilization*, 2019, 34, 533-542]. Homogeneous catalysts, including metal-based complexes and organocatalysts, have demonstrated efficiency but are hindered by limitations such as poor recyclability, challenging separation, and product contamination [Maeda, C. et al., Bifunctional catalysts based on m-phenylene-bridged porphyrin dimer and trimer platforms: synthesis of cyclic carbonates from carbon dioxide and epoxides, *Angewandte Chemie International Edition*, 2015, 54, 1, 134-138; and Comerford, J. W. et al. *Sustainable metal-based catalysts for the synthesis of cyclic carbonates containing five-membered rings*, *Green Chemistry*, 2015, 17, 4, 1966-1987].

In response, heterogeneous catalytic systems have emerged as viable alternatives. Materials such as metal oxides [Yamaguchi, K. et al., Mg—Al mixed oxides as highly active acid-base catalysts for cycloaddition of carbon dioxide to epoxides, *J Am Chem Soc*, 1999, 121, 18, 4526-4527], ionic liquids [Li, F. et al., Chemical fixation of $CO_2$ with Highly Efficient $ZnCl_2$/[BMIm]Br catalyst system, *Tetrahedron Lett*, 2004, 45, 45, 8307-8310; and Shi, X.-L. et al., Conversion of $CO_2$ into organic carbonates over a fiber-supported ionic liquid catalyst in impellers of the agitation system, *ACS Sustain Chem Eng*, 2018, 6, 5, 7119-7127], salen complexes, and porous frameworks have exhibited potential for catalyzing $CO_2$-epoxide cycloaddition reactions. Systems often employ inorganic and polymeric matrices to immobilize active catalytic species; however, random distribution and leaching of catalytic centers remain persistent issues, adversely impacting long-term performance, activity retention, and scalability of the catalysts.

Covalent organic frameworks (COFs), a class of crystalline porous polymers composed of light elements, such as hydrogen (H), boron (B), carbon (C), nitrogen (N), and oxygen (O), have emerged as platforms for heterogeneous catalysis [Ma, H.-C. et al., Pd NPs-Loaded homochiral covalent organic framework for heterogeneous asymmetric catalysis, *Chemistry of Materials*, 2017, 29, 15, 6518-6524]. The ability to tailor topology thereof using molecular precursors connected via diverse linkages such as B—O, C=N, C—N, B—N, N—N, C—O, and C=C enables structural control and functional tunability [Côté, A. P. et al. Porous, crystalline, covalent organic frameworks, *Science*, 2005, 310, 5751, 1166-1170]. High surface area, inherent porosity, and stable covalent architectures facilitate effective transport and interaction with catalytic and substrate molecules, making them attractive hosts for metal nanoparticles in catalysis applications [Basak, A. et al., Covalent organic frameworks as porous pigments for photocatalytic metal-free C—H Borylation, *J Am Chem Soc*, 2023, 145, 13, 7592-7599; and Guo, J. and Jiang, D., Covalent organic frameworks for heterogeneous catalysis: Principle, current status, and challenges, *ACS Cent Sci*, 2020, 6, 6, 869-879].

Among COF architectures, structures constructed using imine (Schiff base) linkages have been explored for metal nanoparticle incorporation; however, imine-based COFs suffer from limited hydrolytic stability and need close spatial proximity of linkers for efficient metal coordination [Ding, S.-Y. et al., Construction of covalent organic framework for catalysis: Pd/COF-LZU1 in Suzuki-Miyaura Coupling Reaction, *J Am Chem Soc*, 2011, 133, 49, 19816-19822].

Attempts to mitigate issues through structural modifications, such as increasing the linker size and introducing bulky substituents, often compromise metal retention due to reduced interaction strength and increased leaching. As such, nitrogen-rich monomers with triazine cores have been employed to form amorphous polymeric networks exhibiting stronger affinity for noble metals and resistance to Ostwald ripening [Modak, A. et al., A Triazine functionalized porous organic polymer: excellent $CO_2$ storage material and support for designing pd nano catalyst for c-c cross-coupling reactions, *J Mater Chem A Mater*, 2014, 2, 30, 11642]. Vulnerability of imine linkages to hydrolysis remains a constraint for practical deployment across diverse catalytic conditions [Qian, C. et al., Toward covalent organic frameworks bearing three different kinds of pores: The strategy for construction and COF-to-COF transformation via heterogeneous linker exchange, *J Am Chem Soc*, 2017, 139, 19, 6736-6743].

To overcome limitations, alternatives to imine linkages have been considered. Olefinic bonds, known for their stability against concentrated Bronsted acids and bases, Lewis acids, and organolithium reagents, have been investigated as potential linkers for COF construction [Lyu, H. et al. Porous crystalline olefin-linked covalent organic frameworks, *J Am Chem Soc*, 2019, 141, 17, 6848-6852]. Design of a chemically and thermally stable COF architecture that integrates a triazine-based nitrogen-rich core with olefinic linkages offers a route for the next generation of heterogeneous catalysts for $CO_2$ fixation applications.

Despite progress in this domain, there remains a need for a catalytically competent, structurally stable, and easily recoverable heterogeneous catalytic system capable of facilitating $CO_2$ conversion under moderate or ambient conditions with high selectivity and reusability. Accordingly, an object of the present disclosure is to provide a method of carbon dioxide fixation, that may circumvent drawbacks and limitations of methods known in the art.

SUMMARY

In an exemplary embodiment, a method of carbon dioxide fixation is described. The method includes contacting a covalent organic framework material with a co-catalyst and an epoxide in the presence of carbon dioxide to form a cyclic carbonate. The covalent organic framework material includes reacted units of a 2,4,6-trimethyl-1,3,5-triazine, reacted units of a 4,4'-biphenyldicarbaldehyde, and palladium nanoparticles. The reacted units of the 2,4,6-trimethyl-1,3,5-triazine and the reacted units of the 4,4'-biphenyldicarbaldehyde form a COF-701, where the palladium nanoparticles are on an outer surface of the COF-701. The co-catalyst is n-tetrabutylammonium bromide.

In some embodiments, the palladium nanoparticles have a diameter of 0.5 to 10 nm.

In some embodiments, the palladium nanoparticles have a diameter of 2 to 5 nm.

In some embodiments, the covalent organic framework material is in the shape of spheres having a diameter of 0.5 to 10 μm.

In some embodiments, the spheres are connected by a common facial aperture.

In some embodiments, the covalent organic framework material is porous, and the COF-701 has a pore width of 0.1 to 2 nm.

In some embodiments, the covalent organic framework material is at least 90 percent by weight (wt. %) stable at a temperature of 400° C. based on an initial weight of the covalent organic framework material.

In some embodiments, the epoxide is selected from the group consisting of 1,2-epoxypropane, 1,2-epoxybutane, 1,2-epoxyhexane, epichlorohydrin, allyl glycidyl ether, styrene oxide, and phenyl glycidyl ether.

In some embodiments, the epoxide is styrene oxide.

In some embodiments, the co-catalyst is an n-tetrabutylammonium salt.

In some embodiments, the contacting occurs at a temperature of 40 to 120° C.

In some embodiments, the contacting occurs at a temperature of 50 to 70° C.

In some embodiments, the contacting occurs for 4 to 14 hours.

In some embodiments, the carbon dioxide is at a pressure of 0.5 to 2 bar.

In some embodiments, a molar ratio of the co-catalyst to the epoxide is 5:1 to 1:5.

In some embodiments, at least 85% of the epoxide is converted to the cyclic carbonate based on a proton nuclear magnetic resonance spectrum.

In some embodiments, 95 to 97% of the epoxide is converted to the cyclic carbonate based on a proton nuclear magnetic resonance spectrum.

In some embodiments, a selectivity for the cyclic carbonate is at least 98% based on an integration of a —CH signal at 4.34 ppm in a proton nuclear magnetic resonance spectrum.

In some embodiments, the method further includes recovering the covalent organic framework material after the contacting, washing the covalent organic framework material, drying the covalent organic framework material under vacuum at a temperature of 80 to 120° C. for 8 to 16 hours, and contacting the covalent organic framework material with the co-catalyst and the epoxide in the presence of carbon dioxide to form the cyclic carbonate.

In some embodiments, after repeating the recovering, washing, drying, and contacting 8 to 10 times, the covalent organic framework material has a yield percentage of the cyclic carbonate of at least 90% of that of an initial yield percentage of the cyclic carbonate of the covalent organic framework material.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
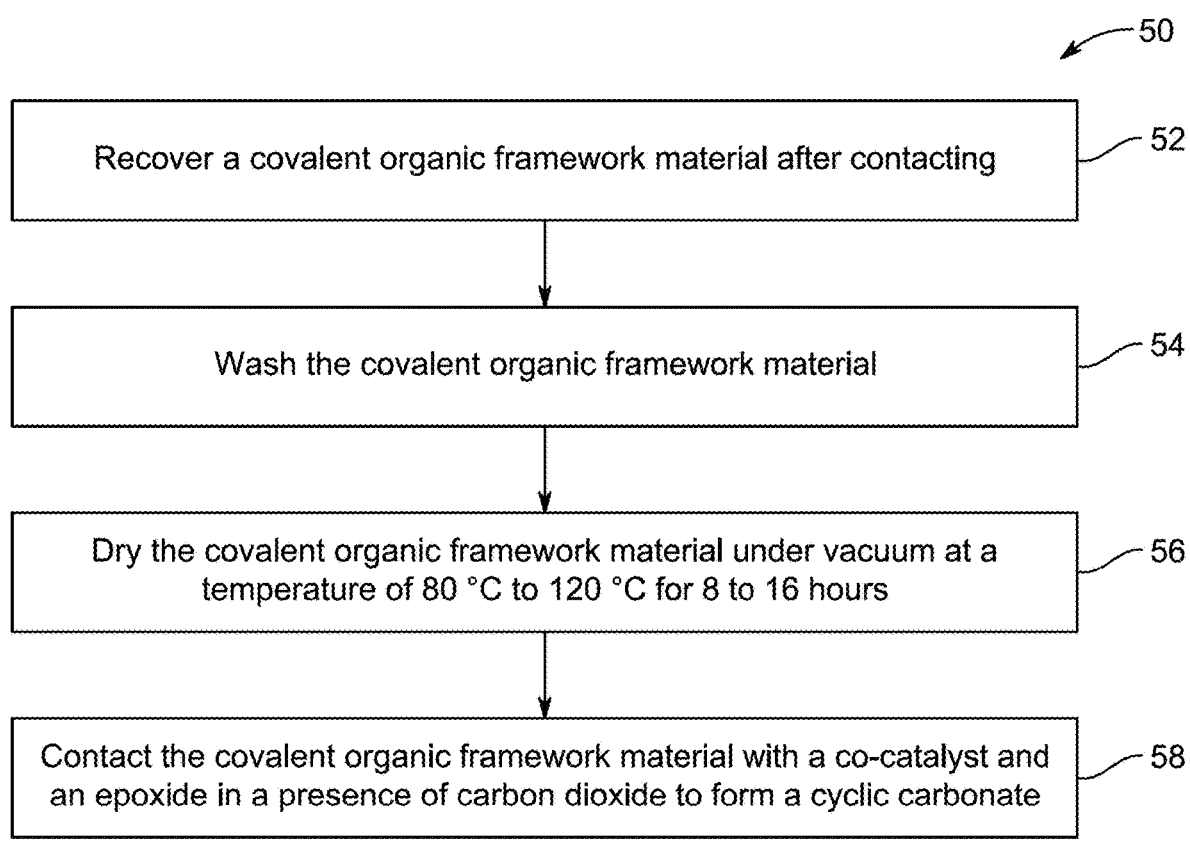
FIG. 1 illustrates an exemplary flow chart for a method of carbon dioxide fixation, according to certain embodiments.

When describing the present disclosure, the terms used are to be construed in accordance with the following definitions, unless a context dictates otherwise.

Embodiments of the present disclosure will now be described more fully hereinafter with reference to the accompanying drawings wherever applicable, in that some, but not all, embodiments of the disclosure are shown.

In the drawings, like reference numerals will be used to designate identical or corresponding parts throughout the several views. Further, as used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term "room temperature" refers to a temperature range of '25±3 degrees Celsius (° C.) in the present disclosure.

As used herein, the term "nanoparticles (NPs)" refers to particles having a particle size of 1 to 500 nanometers (nm).

As used herein, the term "carbon dioxide fixation" refers to chemical incorporation of carbon dioxide into organic molecules, typically through a catalytic reaction, to form stable, value-added compounds.

As used herein, the term "covalent organic framework" refers to a crystalline porous polymeric material composed of light elements linked by covalent bonds in an extended network.

As used herein, the term "co-catalyst" refers to a secondary catalyst used in conjunction with a primary catalyst to enhance the overall efficiency, selectivity, and/or rate of a chemical reaction.

As used herein, the term "cyclic carbonate" refers to a class of organic compounds featuring a five-membered ring containing both carbonate and alkylene groups, typically synthesized via the reaction of $CO_2$ with epoxides.

As used herein, the term "porous" refers to a material characteristic denoting the presence of interconnected voids or channels that allow for the adsorption, diffusion, and/or passage of molecules.

As used herein, the term "pore-width" refers to the diameter or size of the openings within a porous material, which influences molecular access and transport through the structure.

As used herein, the term "proton nuclear magnetic resonance spectrum" refers to a graphical representation of magnetic resonance signals of hydrogen nuclei ($^1H$) in a sample, providing information about molecular structure and environment.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

Aspects of the present disclosure are directed to the synthesis of a nitrogen-rich olefinic covalent organic framework (COF)-based catalytic system embedded with Pd nanoparticles for efficient and selective conversion of $CO_2$ to cyclic carbonates under mild conditions.

A method of carbon dioxide fixation is described. The method includes contacting a covalent organic framework material with a co-catalyst and an epoxide in the presence of carbon dioxide to form a cyclic carbonate.

The covalent organic framework material includes reacted units of a 2,4,6-trimethyl-1,3,5-triazine, reacted units of a 4,4'-biphenyldicarbaldehyde, and palladium nanoparticles. In some embodiments, reacted units of other triazines such as melamine, cyanuric chloride, 2,4-diamino-6-phenyl-1,3,5-triazine, 2,4,6-triethyl-1,3,5-triazine, 2,4,6-tri(tert-butyl)-1,3,5-triazine, 2-chloro-4,6-dimethoxy-1,3,5-triazine, 2,4,6-trimethoxy-1,3,5-triazine, 2,4,6-triethoxy-1,3,5-triazine, 2,4-dichloro-6-methoxy-1,3,5-triazine, 2-amino-4,6-dimethoxy-1,3,5-triazine, 2,4,6-triphenyl-1,3,5-triazine, 2,4-diamino-6-methyl-1,3,5-triazine, 2-hydroxy-4,6-dimethoxy-1,3,5-triazine, 2,4-dimethoxy-6-methyl-1,3,5-triazine, 2,4,6-trimorpholino-1,3,5-triazine, 2,4-dichloro-6-phenyl-1,3,5-triazine, 2,4,6-tris(alkylamino)-1,3,5-triazine, 2,4,6-tris(aryl)-1,3,5-triazine, 2,4-dibromo-6-methoxy-1,3,5-triazine, 2,4,6-tris(ethoxycarbonyl)-1,3,5-triazine, a combination thereof, and the like may be used in place or in combination with reacted units of a 2,4,6-trimethyl-1,3,5-triazine. In some embodiments, reacted units of other carbaldehydes such as terephthalaldehyde, isophthalaldehyde, 1,3,5-tris(4-formylphenyl)benzene, 2,5-dimethoxyterephthalaldehyde, 4-formylbenzoic acid, 3,5-diformylbenzoic acid, 4,4'-diaminobenzene-dialdehyde, naphthalene-2,6-dicarbaldehyde, 9,10-anthracenedicarbaldehyde, pyrene-1,6-dicarbaldehyde, benzene-1,2-dicarbaldehyde, 1,2,4,5-benzenetetracarbaldehyde, triphenylamine-based dialdehyde, 4,4'-formyldiphenyl ether, carbazole-based dialdehyde, fluorene-2,7-dicarbaldehyde, acenaphthene-1,2-dicarbaldehyde, stilbene-4,4'-dicarbaldehyde, thieno[3,2-b]thiophene-2,5-dicarbaldehyde, dibenzothiophene-4,6-dicarbaldehyde, a combination thereof, and the like may be used in place of or in combination with reacted units of a 4,4'-biphenyldicarbaldehyde.

In some embodiments, the covalent organic framework may include other metal nanoparticles such as gold nanoparticles, silver nanoparticles, platinum nanoparticles, nickel nanoparticles, copper nanoparticles, iron nanoparticles, cobalt nanoparticles, ruthenium nanoparticles, rhodium nanoparticles, iridium nanoparticles, zinc nanoparticles, manganese nanoparticles, titanium nanoparticles, vanadium nanoparticles, molybdenum nanoparticles, chromium nanoparticles, gallium nanoparticles, tin nanoparticles, aluminum nanoparticles, bismuth nanoparticles, a combination thereof, and the like may be used in place of or in combination with the palladium nanoparticles.

In some embodiments, the palladium nanoparticles may be derived from a palladium salt including, but not limited to, palladium(II) chloride, palladium(II) acetate, palladium(II) bromide, palladium(II) iodide, palladium(II) sulfate, palladium(II) fluoride, palladium(II) carbonate, palladium(II) nitrate, palladium(II) oxide, palladium(II) tetrafluoroborate, palladium(II) trifluoroacetate, palladium(II) triflate, palladium(II) bis(benzonitrile) dichloride, palladium(II) cyanide, palladium(II) ethylhexanoate, palladium(II) hydroxide, palladium(II) stearate, palladium(II) propionate, palladium(II) succinate, palladium(II) perchlorate, palladium(II) formate, a combination thereof, and the like. In a preferred embodiment, palladium salt is palladium(II) nitrate.

The reacted units of the 2,4,6-trimethyl-1,3,5-triazine and the reacted units of the 4,4'-biphenyldicarbaldehyde form COF-701. COF-701 is formed through a condensation reaction between 2,4,6-trimethyl-1,3,5-triazine and 4,4'-biphenyldicarbaldehyde, where the aldehyde groups react with the nitrogen-containing triazine core to create an ordered, porous framework. The triazine unit serves as a three-armed node, while the biphenyl dialdehyde acts as a rigid linear linker, resulting in a crystalline covalent organic framework with high surface area, thermal stability, and applications in gas storage, separation, and catalysis. The palladium nanoparticles are on an outer surface of the COF-701. In some embodiments, accessible functional groups and high surface area facilitate uniform dispersion and strong interactions of the palladium nanoparticles with the COF-701.

In some embodiments, the palladium nanoparticles have a diameter of 0.5 to 10 nm, preferably 1 to 9 nm, preferably 2 to 8 nm, preferably 3 to 7 nm, preferably 4 to 6 nm, and preferably 4.5 to 5.5 nm. In some embodiments, the palladium nanoparticles have a diameter of 2 to 5 nm, preferably 2.5 to 4.5 nm, and preferably 3 to 4 nm.

The co-catalyst is n-tetrabutylammonium bromide. In some embodiments, the co-catalyst is n-tetrabutylammonium salt. Suitable examples of the n-tetrabutylammonium salt may include, but are not limited to, n-tetrabutylammonium chloride, n-tetrabutylammonium bromide, n-tetrabutylammonium iodide, n-tetrabutylammonium fluoride, n-tetrabutylammonium hydroxide, n-tetrabutylammonium nitrate, n-tetrabutylammonium acetate, n-tetrabutylammonium hydrogen sulfate, n-tetrabutylammonium dihydrogen phosphate, n-tetrabutylammonium perchlorate, n-tetrabutylammonium carbonate, n-tetrabutylammonium bicarbonate, n-tetrabutylammonium cyanide, n-tetrabutylammonium azide, n-tetrabutylammonium thiocyanate, n-tetrabutylammonium hexafluorophosphate, n-tetrabutylammonium tetrafluoroborate, n-tetrabutylammonium tosylate, n-tetrabutylammonium triflate, n-tetrabutylammonium salicylate, n-tetrabutylammonium benzoate, a combination thereof, and the like.

In some embodiments, the epoxide is selected from the group consisting of 1,2-epoxypropane, 1,2-epoxybutane, 1,2-epoxyhexane, epichlorohydrin, allyl glycidyl ether, styrene oxide, and phenyl glycidyl ether. In an embodiment, the epoxide is styrene oxide. In other embodiments, other epoxides including, but not limited to, ethylene oxide, propylene oxide, butylene oxide, cyclohexene oxide, glycidol, 1,2-epoxydodecane, 1,2-epoxyoctane, 1,2-epoxynonane, vinyl cyclohexene monoxide, isobutylene oxide, glycidyl methacrylate, glycidyl acetate, glycidyl butyrate, trimethylene oxide, a combination thereof, and the like may also be used.

In some embodiments, a molar ratio of the co-catalyst to the epoxide is 5:1 to 1:5, preferably 4:1 to 1:4.5, preferably 3:1 to 1:4, preferably 2:1 to 1:3.5, preferably 1:1 to 1:3, more preferably 1:1.5 to 1:2.5, and yet more preferably about 1:2. In a preferred embodiment, a molar ratio of the co-catalyst to the epoxide is 1:2.

In some embodiments, contacting the covalent organic framework material with the co-catalyst and the epoxide occurs at a temperature of 40 to 120° C., preferably 50 to 110° C., preferably 60 to 100° C., preferably 70 to 90° C., and preferably 75 to 85° C. In some embodiments, the contacting occurs at a temperature of 50 to 70° C., preferably 55 to 65° C., and more preferably about 60° C.

In some embodiment, contacting the covalent organic framework material with the co-catalyst and the epoxide occurs for 4 to 14 hours, preferably 4.5 to 13 hours, preferably 5 to 12 hours, preferably 5.5 to 11 hours, preferably 6 to 10 hours, preferably 7 to 9 hours, and preferably 7.5 to 8.5 hours. In a preferred embodiment, the contacting occurs for about 6 hours. In some embodiments, the carbon dioxide is at a pressure of 0.5 to 2 bar, preferably 0.6 to 1.8 bar, preferably 0.7 to 1.6 bar, preferably 0.8 to 1.4 bar, more preferably 0.9 to 1.2 bar, and yet more preferably about 1 bar. In a preferred embodiment, the carbon dioxide is at a pressure of 1 bar.

In some embodiments, the covalent organic framework material consists of a sheet morphology, preferably nanosheets, although other morphologies such as nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nano-urchins, nanoflowers, nanostars, tetrapods, and their mixtures thereof, and the like are also possible. In a preferred embodiment, the covalent organic framework material is in the shape of spheres.

In some embodiments, the covalent organic framework material is in the shape of spheres having a diameter of 0.5 to 10 µm, preferably 1 to 9 µm, preferably 2 to 8 µm, preferably 3 to 7 µm, preferably 4 to 6 µm, and preferably 4.5 to 5.5 µm. In a preferred embodiment, the covalent organic framework material is in the shape of spheres having a diameter of 1 to 5 µm, preferably 2 to 4 µm, and preferably 2.5 to 3.5 µm. In a preferred embodiment, the spheres are connected by a common facial aperture. In some embodiments, the spheres are connected by a common facial surface. In some embodiments, the spheres are connected by a common boundary. In some embodiments, a common facial aperture is an edge of a sphere. In an embodiment, the covalent organic framework material is in the shape of spheres and a first sphere is connected to a second sphere through a common edge between the first sphere and the second sphere. In some embodiments, connected may refer to electrostatic interactions, covalent bonds, hydrogen bonds, London dispersion forces, a combination thereof, and the like. In some embodiments, the spheres are connected by more than one common facial aperture. In an embodiment, the covalent organic framework material is in the shape of spheres and a first sphere is connected to a second sphere and a third sphere through a common edge between the first sphere and the second sphere and a common edge between the first sphere and the third sphere.

In some embodiments, the covalent organic framework material is porous. A porous material is the one that forms a porous bulk solid. Pores may be micropores, mesopores, macropores, and/or a combination thereof. In some embodiments, pores exist in the bulk material, but not necessarily in the molecular structure of the material. The term "microporous" means that a nanocomposite has pores with an average pore width (i.e., diameter) of less than 2 nm. The term "mesoporous" means the pores of a nanocomposite have an average pore width of 2-50 nm. The term "macroporous" means the pores of a nanocomposite have an average pore width larger than 50 nm. Pore size may be determined by methods including, but not limited to, gas adsorption (e.g., $N_2$ adsorption), mercury intrusion porosimetry, and imaging techniques such as scanning electron microscopy (SEM), and X-ray computed tomography (XRCT). In some embodiments, the covalent organic framework material is porous, and the COF-701 has a pore width of 0.1 to 2 nm, preferably 0.2 to 1.9 nm, preferably 0.3 to 1.8 nm, preferably 0.4 to 1.7 nm, preferably 0.5 to 1.6 nm, preferably 0.6 to 1.5 nm, preferably 0.7 to 1.4 nm, preferably 0.8 to 1.3 nm, more preferably 0.9 to 1.2 nm, and yet more preferably 1 to 1.1 nm. In a preferred embodiment, the pore width is about 1.1 nm.

In some embodiments, the covalent organic framework material is at least 90 percent by weight (wt. %) stable, preferably at least 91 wt. % stable, preferably at least 92 wt. % stable, preferably at least 93 wt. % stable, preferably at least 94 wt. % stable, and preferably at least 95 wt. % stable at a temperature of 400° C. based on an initial weight of the covalent organic framework material. In a preferred embodiment, 95 wt. % COF is stable at a temperature of 400° C. based on an initial weight of the covalent organic framework material.

In some embodiments, at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% of the epoxide is converted to the cyclic carbonate based on a proton nuclear magnetic resonance spectrum. In some embodiments, the epoxide is styrene oxide and 95 to 97%, preferably 95.5 to 96.5%, and more preferably about 96% of the epoxide is converted to the cyclic carbonate based on a proton nuclear magnetic resonance spectrum.

In some embodiments, the selectivity for the cyclic carbonate is at least 98%, preferably at least 98.5%, preferably at least 99%, and preferably 99.5% based on an integration of a —CH signal at 4.34 ppm in a proton nuclear magnetic resonance spectrum. In a preferred embodiment, selectivity for the cyclic carbonate is about 100% based on an integration of a —CH signal at 4.34 ppm in a proton nuclear magnetic resonance spectrum.

FIG. 1 illustrates a schematic flow chart of a method 50 for reusing the covalent organic framework (COF) material. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 includes recovering the covalent organic framework material (also referred to as a catalyst) after the contacting. In some embodiments, recovering the COF material may include adding solvents or reagents such as methanol, ethanol, acetonitrile, dimethylformamide, dimethyl sulfoxide, toluene, hexane, diethyl ether, acetone, water, tetrahydrofuran, isopropanol, benzene, ethyl acetate, butanol, xylene, formic acid, dichloromethane, propanol, nitromethane, a combination thereof, and the like to the covalent organic framework material, the co-catalyst, the epoxide, and carbon dioxide (also referred to as a reaction mixture). In a preferred embodiment, the reaction mixture is diluted with chloroform, and the catalyst is recovered by centrifugation (5000 rpm).

At step 54, the method 50 includes washing the covalent organic framework material. In some embodiments, washing the COF material may include, but is not limited to, the use of ethanol, isopropanol, acetonitrile, water, acetone, dimethylformamide, dimethyl sulfoxide, toluene, hexane, tetrahydrofuran, dichloromethane, ethyl acetate, diethyl ether, propanol, butanol, formic acid, benzene, xylene, nitromethane, chloroform, a combination thereof, and the like. In a preferred embodiment, washing the COF material is done with methanol.

At step 56, the method 50 includes drying the covalent organic framework material under vacuum at a temperature of 80 to 120° C., preferably 85 to 115° C., preferably 90 to 110° C., and more preferably 95 to 105° C. for 8 to 16 hours, preferably 9 to 15 hours, preferably 10 to 14 hours, and more preferably 11 to 13 hours. In a preferred embodiment, drying the covalent organic framework material under vacuum at a temperature of about 100° C. for about 12 hours.

At step 58, the method 50 includes contacting the covalent organic framework material with the co-catalyst and the epoxide in the presence of carbon dioxide to form the cyclic carbonate.

In some embodiments, the covalent organic framework material is contacted at a temperature ranging from 40 to 120° C., preferably 45 to 100° C., preferably 50 to 70° C., more preferably 55 to 65° C., and more preferably about 60° C. In some embodiments, the covalent organic framework material is contacted with the co-catalyst and the epoxide for 4 to 14 hours, preferably 4.5 to 12 hours, preferably 5 to 10 hours, more preferably 5.5 to 8 hours, and yet more preferably about 6 hours.

In some embodiments, after repeating the recovering, washing, drying, and contacting 8 to 10 times, preferably 9 times, the covalent organic framework material has a yield percentage of the cyclic carbonate of at least 90%, preferably at least 91%, preferably at least 92%, preferably at least 93%, preferably at least 94%, preferably at least 95%, and preferably at least 96% of that of an initial yield percentage of the cyclic carbonate of the covalent organic framework material.

The following examples are provided solely for illustration and are not to be construed as limitations of the present disclosure, as many variations thereof are possible without departing from the spirit and scope of the present disclosure.

EXAMPLES

The following examples describe and demonstrate a method for fixing carbon dioxide into cyclic carbonates using heterogeneous catalysts. The examples are provided solely for illustration and are not to be construed as limitations of the present disclosure, as many variations thereof are possible without departing from the spirit and scope of the present disclosure.

Example 1: Materials 2,4,6-trimethyl-1,3,5-triazine (TMT) and 4,4'-biphenyldicarbaldehyde (BPDA) were purchased from BLD pharm and TCI chemicals, respectively, to use as linkers for COF synthesis. Mesitylene, 1,4-dioxane, acetonitrile, and tetrafluoroacetic acid were used as received from Sigma-Aldrich. Acetone and methanol obtained from TCI chemical were used as washing solvent. Carbon dioxide (99.9%) was supplied by Abdullah Hashim Company, Dammam, KSA. All the chemicals were used as received without any further purification.

Example 2: Synthesis of COF-701

COF-701, an unsubstituted olefinic COF, was synthesized in a Schlenk Tube apparatus. TMT (0.049 mmol) and BPDA (0.075 mmol) were added in a clean and dry Schlenk tube (ST) with an inner empty volume of 10 mL. Mesitylene (0.45 mL), 1,4-dioxane (0.45 mL), and acetonitrile (0.025 mL) were added to the ST followed by the addition of acid catalyst trifluoroacetic acid (0.20 mL). After placing all the components, the openings of Schlenk tube were closed and then the tube was flash-frozen at 77 K (liquid $N_2$ bath). The whole system was evacuated by three freeze-pump-thaw cycles. The mixture was sonicated for homogeneous mixing before placing it inside an oven for 3 days at 150° C. After 72 hours, a yellow precipitate was noticed at the bottom of the tube. The ST was allowed to cool to room temperature and the powder was collected by filtration. The crude product was washed thoroughly with methanol and acetone each for 3 days to remove impurities. The product was heated at 120° C. for 12 h under vacuum to yield the final product.

Example 3: Encapsulation of Pd-Nanoparticle in COF-701 (Pd-NPs@COF-701)

COF-701 (150 mg) was mixed with palladium nitrate (100 mg) in a flask containing 30 mL methanol with stirring at room temperature. The resulted dark green solid was collected by centrifugation and washed with acetonitrile and subsequently dried before reduction with $NaBH_4$. The dried solid was mixed with NaBH₄ in 30 mL water for 5 h with continuous stirring. After complete reduction, a dark black solid was obtained which was washed with acetonitrile and ethanol. Washed products were dried under air and used for characterization and catalysis application.

Example 4: Characterizations of COF-701 and Pd-NPs@COF-701

Crystallographic data of the COF-701 was recorded over the 2θ range of 3° and 400 at a scanning rate of 2° per minute, using a Rigaku MiniFlex diffractometer, which was equipped with Cu-Kα radiation (λ=1.540 Å). Attenuated total reflectance Fourier-transform infrared (ATR-FTIR) spectroscopy was performed for COF-701, TMT, BPDA and Pd-NP attached COF-701 on Nicolet 6700 spectrometer. Brunauer-Emmett-Teller (BET) method was applied to evaluate the surface area and pore size of the COF-701 from the adsorption isotherm. Nitrogen ($N_2$) adsorption isotherm of the COF-316 was recorded using Quantachrome Autosorb iQ (ASIQ000-4, USA). Field emission scanning electron microscopy (FESEM, Tescan Lyra-3 Dual Beam instrument) equipped with an energy dispersive spectrometer (EDX), Oxford Instruments, was used to determine the morphology of the synthesized COF-701. Inductively coupled plasma mass spectrometry (ICP-MS) was conducted in Thermo Scientific XSeries 2 ICP-MS of the Pd-NPs encapsulated sample to evaluate the percentage of Pd loading.

Example 5: Catalytic Cycloaddition of $CO_2$

Completely dried palladium nanoparticles on COF-701 (Pd-NPs@COF-701) material having a mass around 25 milligrams (mg), n-tetrabutylammonium bromide (TBABr) at around 5.0 millimole (mmol), and epoxide at about 10.0 mmol were added to a 50 mL size Schlenk tube at room temperature. 1 bar of $CO_2$ was introduced using a balloon and the reaction mixture was allowed to stir at 60° C. for 6 h. Post completion, the mixture was cooled to room temperature. The reaction mixture was diluted with chloroform and centrifuged to separate the catalyst (Pd-NPs@COF-701). An organic layer was concentrated and passed through a short silica column and eluted with an ethyl acetate/hexane mixture. Pure form of the respective cyclic carbonates was dried and taken for analysis by proton and carbon nuclear magnetic resonance ($^1$H NMR and $^{13}$C NMR).

A selectivity of the products synthesized herein, were analyzed using $^1$H NMR spectroscopy of the product without any purification, based on the integration of the CH signal at the 4.34 parts per million (ppm) of the cyclic ring in the styrene carbonate.

A leaching test was performed by the hot filtration method. During the leaching test, the catalytically active particles were removed after 2 hours from the reaction by filtration through a hot frit, and the filtrate was monitored for continued activity. It was found that the reaction did not proceed indicating that no catalytically active metals leached from the Pd-NPs@COF-701 into the filtrate.

To reuse the Pd-NPs@COF-701 after completion of the reaction, the reaction mixture was diluted with chloroform, and the catalyst was recovered by centrifugation at 5000 revolutions per minute (rpm). Recovered Pd-NPs@COF-701 was repeatedly washed with methanol (5 mL) three times to remove any remaining epoxides and TBABr and dried under vacuum at 100° C. overnight. The reaction conditions were kept the same as used in the first cycle.

Figure 2A:
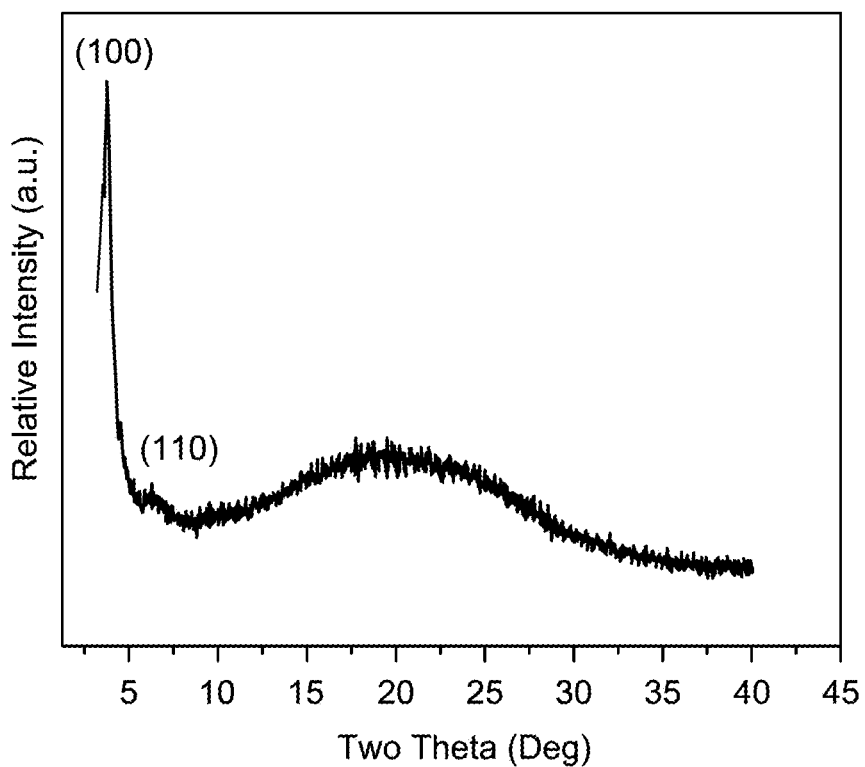
FIG. 2A illustrates a powder X-ray diffraction (pXRD) pattern of COF-701, according to certain embodiments.

The yellow product was collected following complete washing and drying procedures. The product was analyzed to confirm the formation of a new olefinic linkage and to assess a crystallinity thereof. Crystallographic information pertaining to the synthesized covalent organic frameworks (COFs) was recorded and is presented as an X-ray diffraction (XRD) pattern in FIG. 2A. The XRD analysis revealed a low-angle intense peak at approximately 3.6°, corresponding to the strong (100) reflection characteristic of an hcb topology with a space group of P63/m. The observed reflection demonstrates a successful synthesis of an ordered stacking of a hexagonal framework in an AB staggered mode, creating a rhombic channel along the crystallographic C-axis. Furthermore, the stacking of the hexagonal framework with aromatic rings and the newly formed olefinic linkages was observed to generate intense π-π interactions. A broad peak appearing in a range of approximately 22° to 26°, corresponding to the (001) plane, substantiates the presence of interlayer interactions between consecutive COF layers.

Figure 2B:
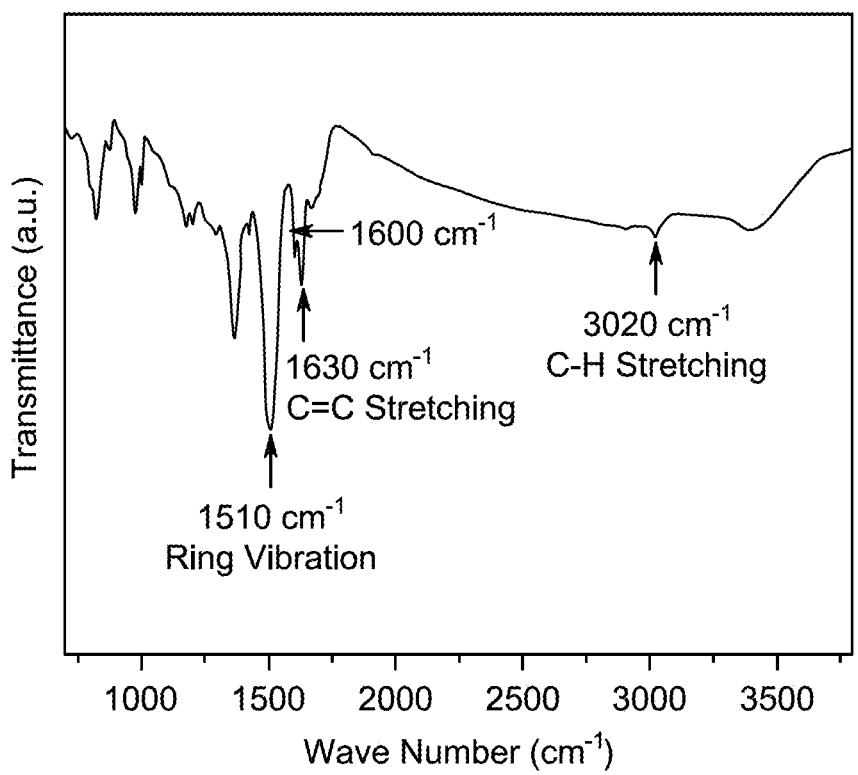
FIG. 2B illustrates a Fourier-transform infrared (FTIR) spectrum of COF-701, according to certain embodiments.

Fourier-transform infrared (FTIR) spectroscopy was performed to verify the formation of a new covalent linkage between the two starting materials, namely 2,4,6-trimethyl-1,3,5-triazine (TMTA) and 4,4'-biphenyldicarbaldehyde (BPDA), and to confirm the disappearance of characteristic peaks associated with the participating functional groups of the starting materials, as shown in FIG. 2B. In the synthesized COF-701 material, a C=C olefinic linkage was formed through aldol condensation between the methyl group of TMTA and the aldehyde group of BPDA [Lyu, H. et al., Porous crystalline olefin-linked covalent organic frameworks, *J Am Chem Soc*, 2019, 141, 17, 6848-6852, which is incorporated herein by reference in its entirety]. The formation of an unsubstituted olefinic (—CH=CH—) linkage was confirmed by comparative analysis of the FTIR spectra of the final COF-701 product and the corresponding starting materials. A new absorbance peak at 1630 cm$^{-1}$ observed in the FTIR spectrum of COF-701 confirms the formation of the —CH=CH— bond, which is absent in the spectra of the starting materials [Hoque, B. et al., Improving the extraction performance of polymer inclusion membranes by cross-linking their polymeric backbone, *React Funct Polym*, 2021, 160, 104813, which is incorporated herein by reference in its entirety]. In addition, the disappearance of the characteristic C=O stretching peak at 1680 cm$^{-1}$, indicative of the —CHO functional group in BPDA, further supports the participation of aldehyde functionalities in the aldol condensation reaction. Peaks identified at 1510 cm$^{-1}$ and 1600 cm$^{-1}$ correspond to skeletal vibrations of the triazine aromatic ring [Purushothaman, R. and Vaitinadin, H. S., Inclusion of covalent triazine framework into fluorinated polyimides to obtain composites with low dielectric constant, *J Appl Polym Sci*, 2020, 137, 37, which is incorporated herein by reference in its entirety]. Collectively, the FTIR data confirm the successful formation of olefinic linkages and the preservation of the triazine core within the COF-701 framework.

Figure 2C:
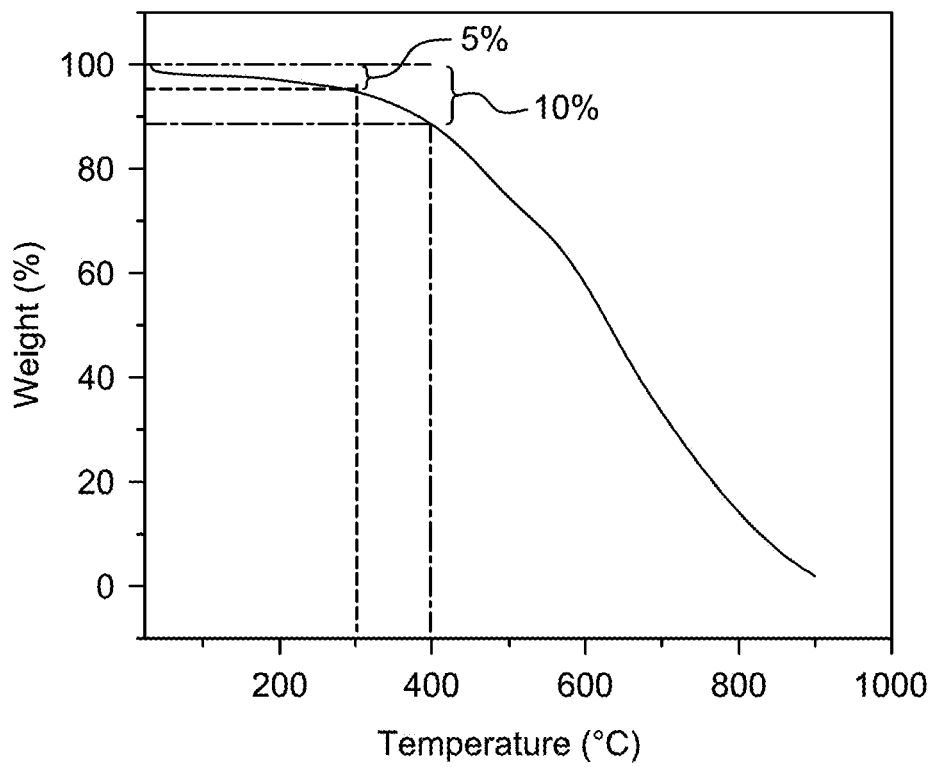
FIG. 2C illustrates a thermogravimetric analysis (TGA) curve of COF-701, according to certain embodiments.

Thermal stability analysis of the synthesized COF-701 was conducted and is depicted in FIG. 2C. The olefinic COF-701 was synthesized through the formation of C=C covalent bonds, characterized by a bond energy of 145.12 kcal/mol. Thermal stability of COF-701 is higher than that of the starting materials, such as TMTA having a melting point of 60° C. and a boiling point of 155° C. The thermal gravimetric analysis indicated that approximately 5% weight loss occurred upon heating to 300° C., with an additional 5% weight loss observed upon further heating to 400° C. The initial 5% weight loss is attributed to the release of trapped washing solvents, which may alternatively be removed via supercritical $CO_2$ drying techniques. The subsequent 5% weight loss between 30° and 400° C. results from the breakdown of incomplete framework extension arms. The bond energy of a C=C linkage (145.12 kcal/mol) is equivalent to the thermal energy generated by heating to 473 K. The COF-701 material was observed to retain a structural integrity up to temperatures exceeding 200° C., owing to the hexagonal framework formation and the presence of interlayer π-π stacking interactions. Such interactions enhance the thermal stability of COF-701, sustaining the framework up to 400° C., beyond which major degradation of the framework is observed.

Figure 3A:
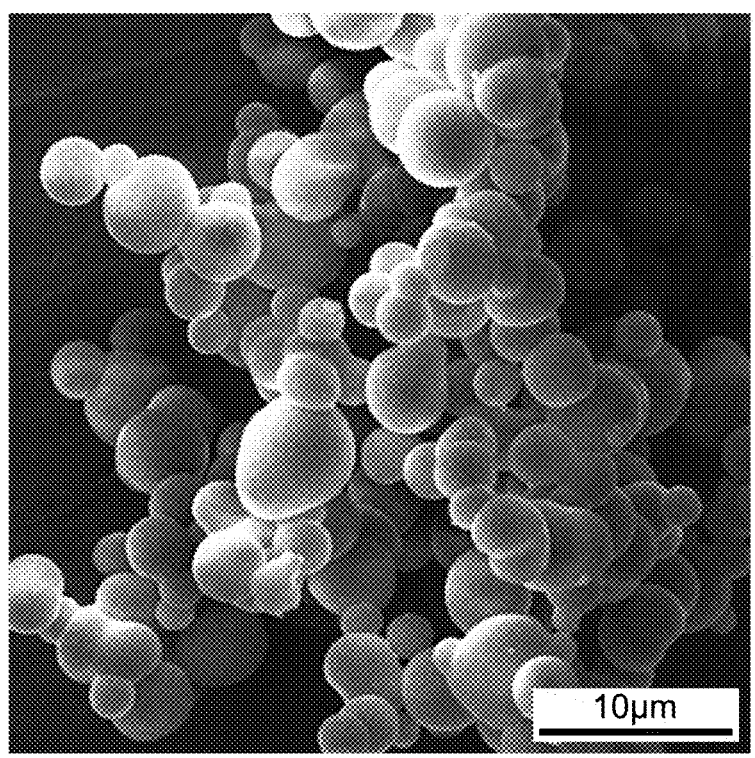
FIG. 3A is a scanning electron microscopy (SEM) image of COF-701 with a scale of 10 μm, according to certain embodiments.
Figure 3B:
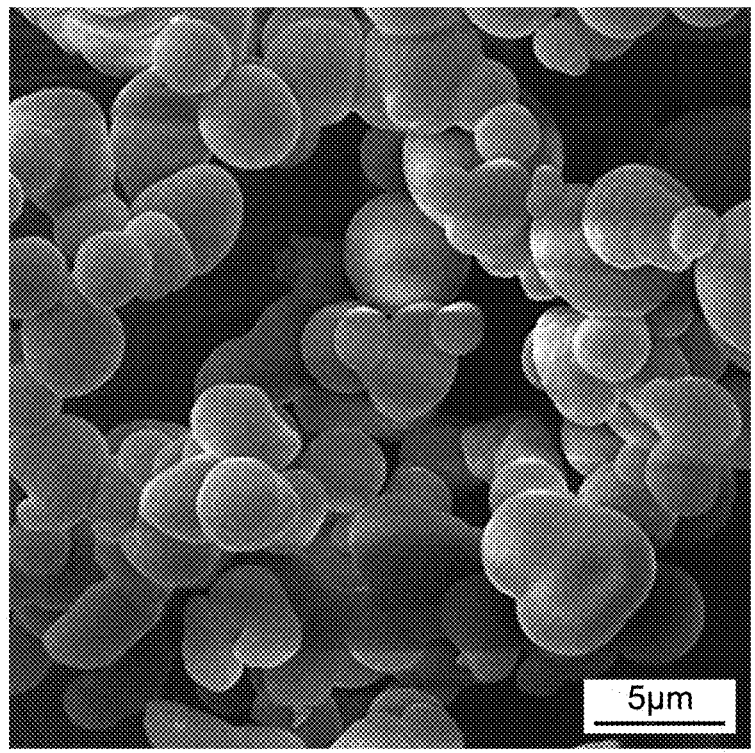
FIG. 3B is an SEM image of COF-701 with a scale of 5 μm, according to certain embodiments.
Figure 3C:
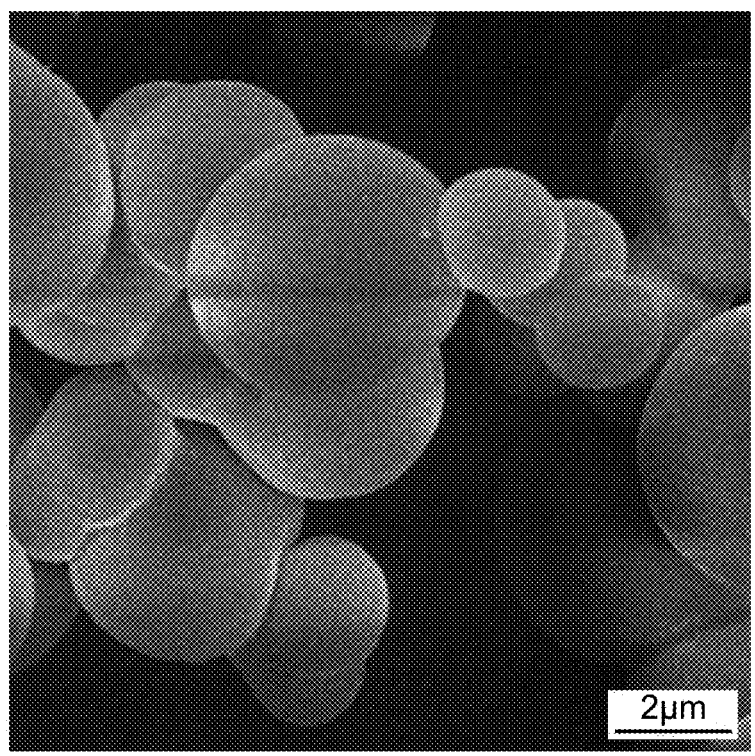
FIG. 3C is an SEM image of COF-701 with a scale of 2 μm, according to certain embodiments.

Surface morphology analysis of the synthesized covalent organic framework (COF) particles revealed a three-dimensional spherical growth pattern. As illustrated in FIG. 3A, a scanning electron microscopy (SEM) image depicts a 40 μm×40 μm area populated by COF spheres of varying diameters, which are connected by shared facial apertures. Formation of spherical morphology from an initial sheet-like structure was observed. Specifically, COF sheets of varying dimensions and curvatures were observed to converge and merge at respective boundary regions thereof, intersecting at different angles to yield spherical particles. The resulting diameter of the nanospheres is influenced by both the length of the individual COF sheets and the curvature present at their merging boundaries, where sheets from multiple directions intersect. As shown in FIGS. 3B-3C, the diameter of the resulting COF spheres ranges from approximately 1 to 5 μm.

Figure 3D:
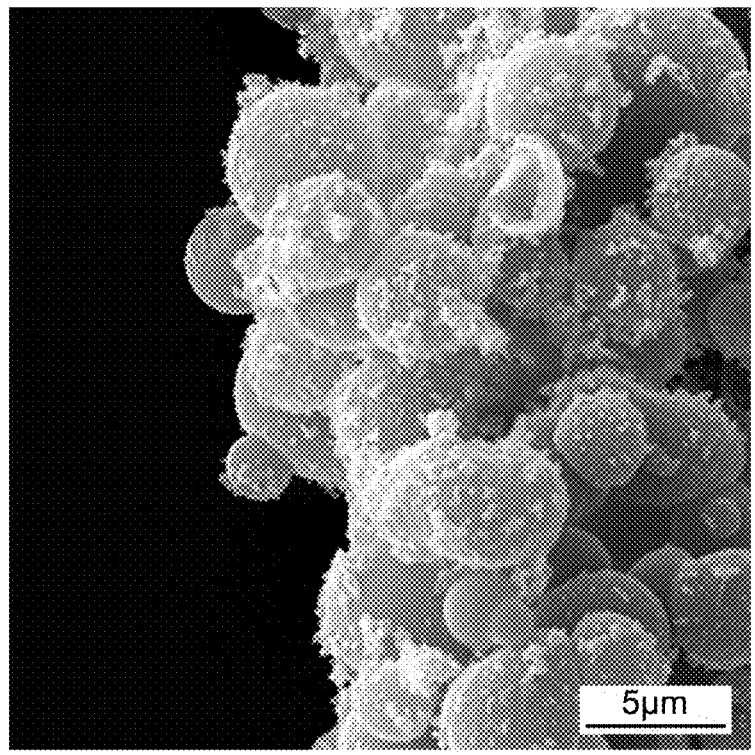
FIG. 3D is an SEM image of Pd-NP@COF-701 with a scale of 5 μm, according to certain embodiments.
Figure 3E:
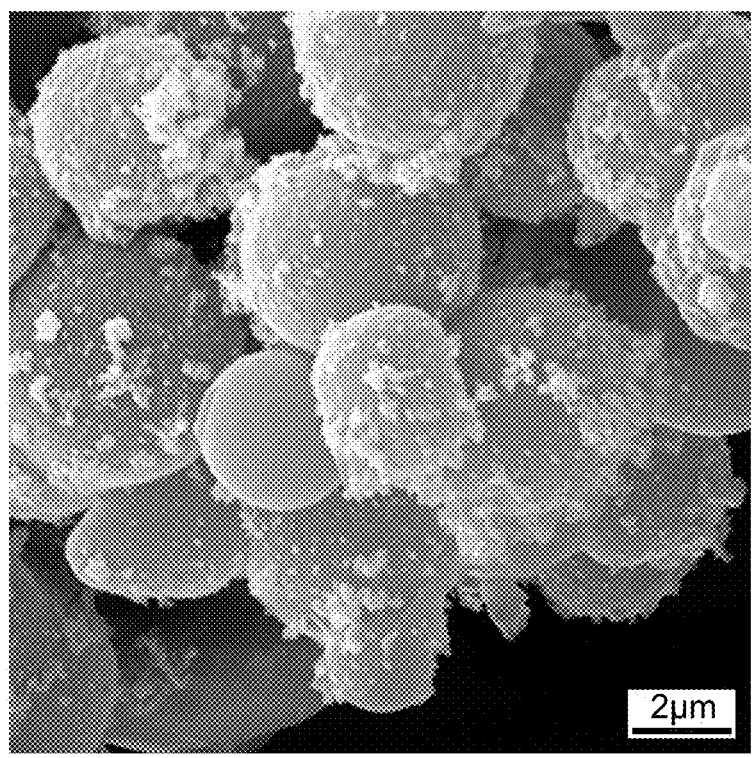
FIG. 3E is an SEM image of Pd-NP@COF-701 with a scale of 2 μm, according to certain embodiments.
Figure 3F:
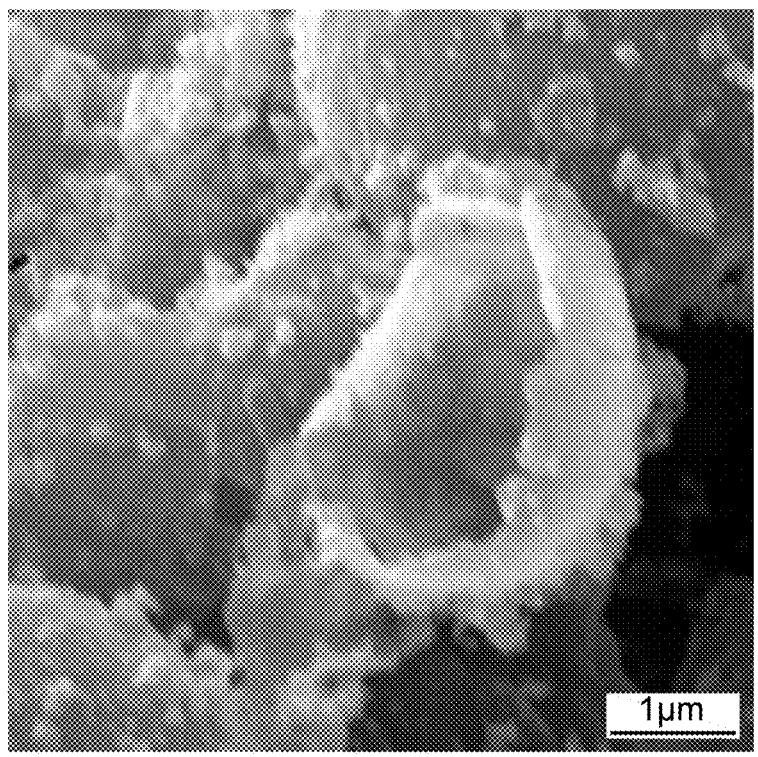
FIG. 3F is an SEM image of Pd-NP@COF-701 with a scale of 1 μm, according to certain embodiments.

The spherical morphology observed in the pristine COF material was found to be retained in the palladium nanoparticle-encapsulated COF (Pd-NP@COF). As seen in FIGS. 3D-3F, palladium nanoparticles are localized and anchored primarily on the outer surface of the spherical COF particles, in regions where coordination interactions with the triazine moiety are structurally feasible. Triazine functional groups facilitate the reduction of Pd ions to form nanoparticles and further stabilize the nanoparticles through coordinate interactions.

Formation of spherical COF particles and the dispersion of palladium nanoparticles (Pd-NPs) were further evaluated through high-resolution transmission electron microscopy (HR-TEM) imaging of both the pristine COF and the Pd-encapsulated COF (Pd-NP@COF). Examination of the HRTEM micrographs support morphological observations, particularly the hierarchical assembly of COF sheets into spherical architectures and the subsequent deposition of Pd nanoparticles on the surface of such structures.

Figure 4A:
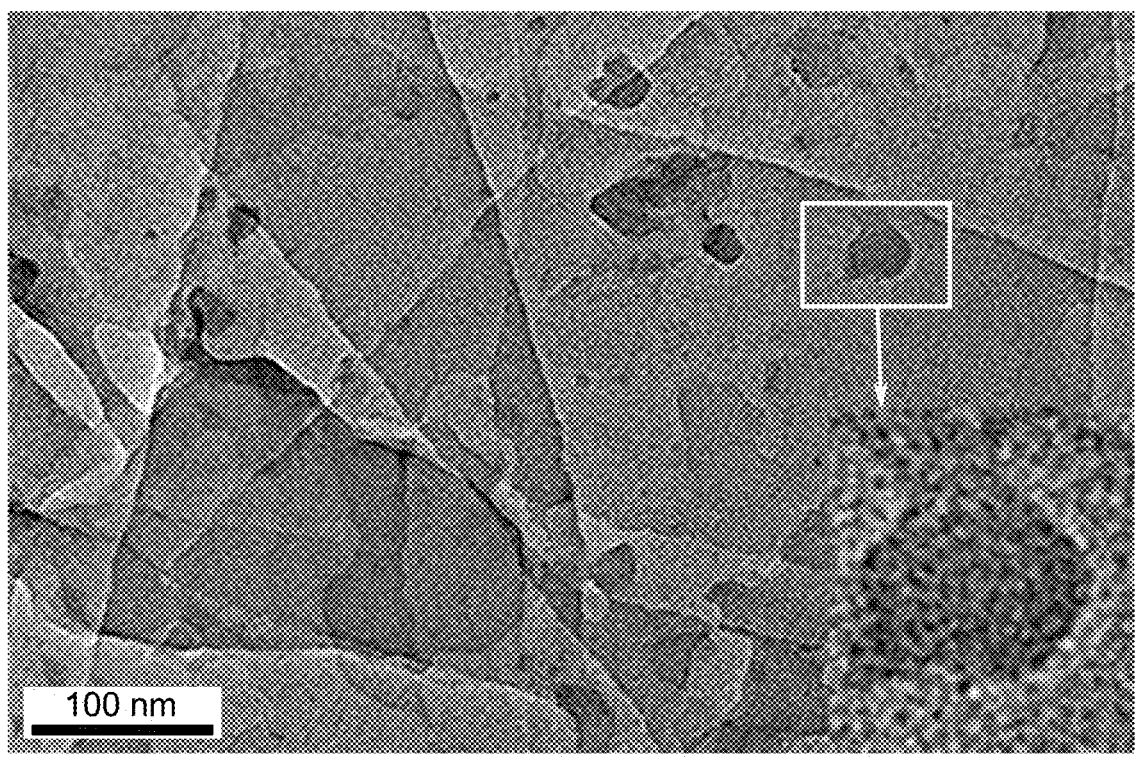
FIG. 4A is a transmission electron microscopy (TEM) image of COF-701 with a scale of 100 nm, according to certain embodiments.
Figure 4B:
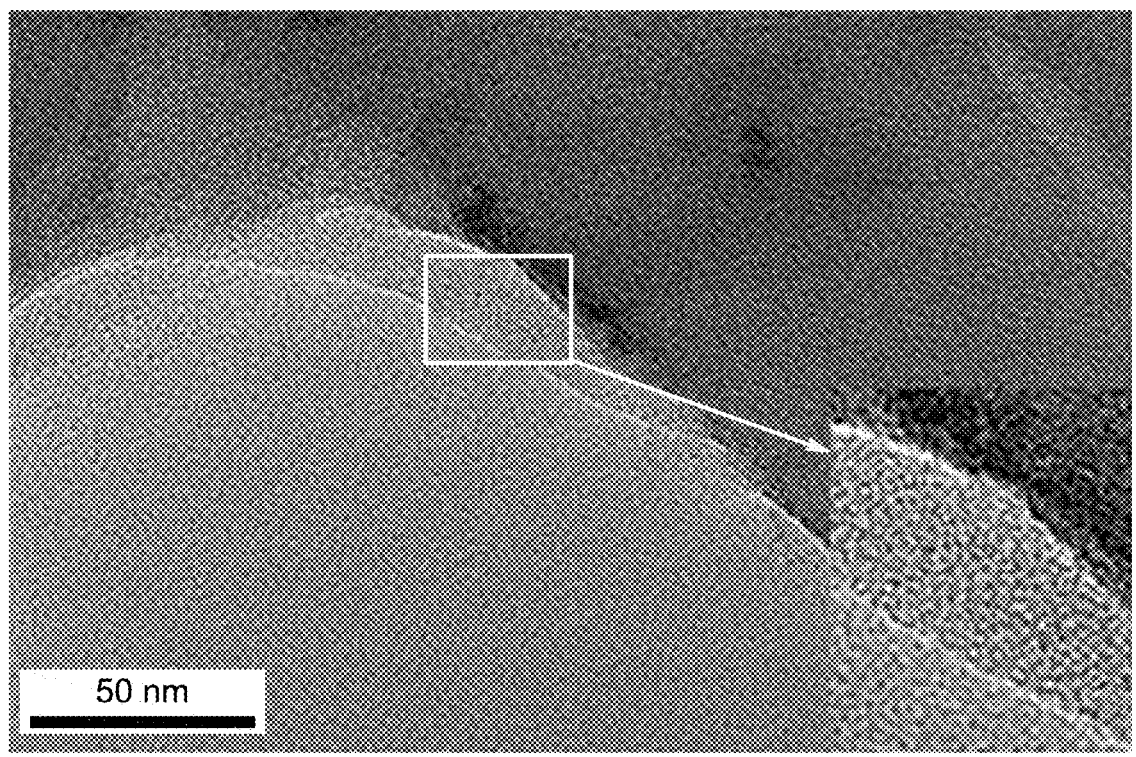
FIG. 4B is a TEM image of COF-701 with a scale of 50 nm, according to certain embodiments.
Figure 4C:
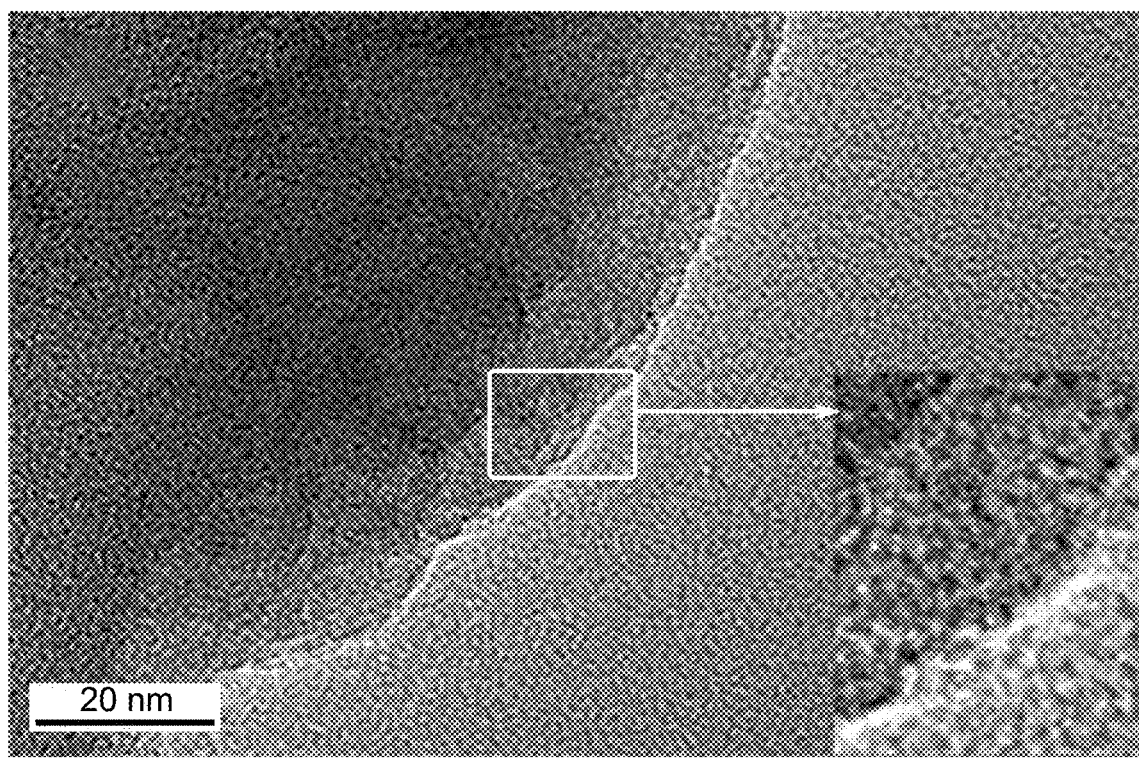
FIG. 4C is a TEM image of COF-701 with a scale of 20 nm, according to certain embodiments.

As illustrated in FIGS. 4A-4C, the parent COF material exhibits a layer-by-layer assembly of hexagonally structured sheets, with observable curvature emerging at the sheet edges. These curvatures are attributed to heterogeneous interactions between stacked sheets of varying lateral dimensions, wherein the interaction intensity is higher at the periphery than at the central regions. This differential interaction among adjacent layers, located above or below a given plane, results in bent sheet conformations.

Figure 4D:
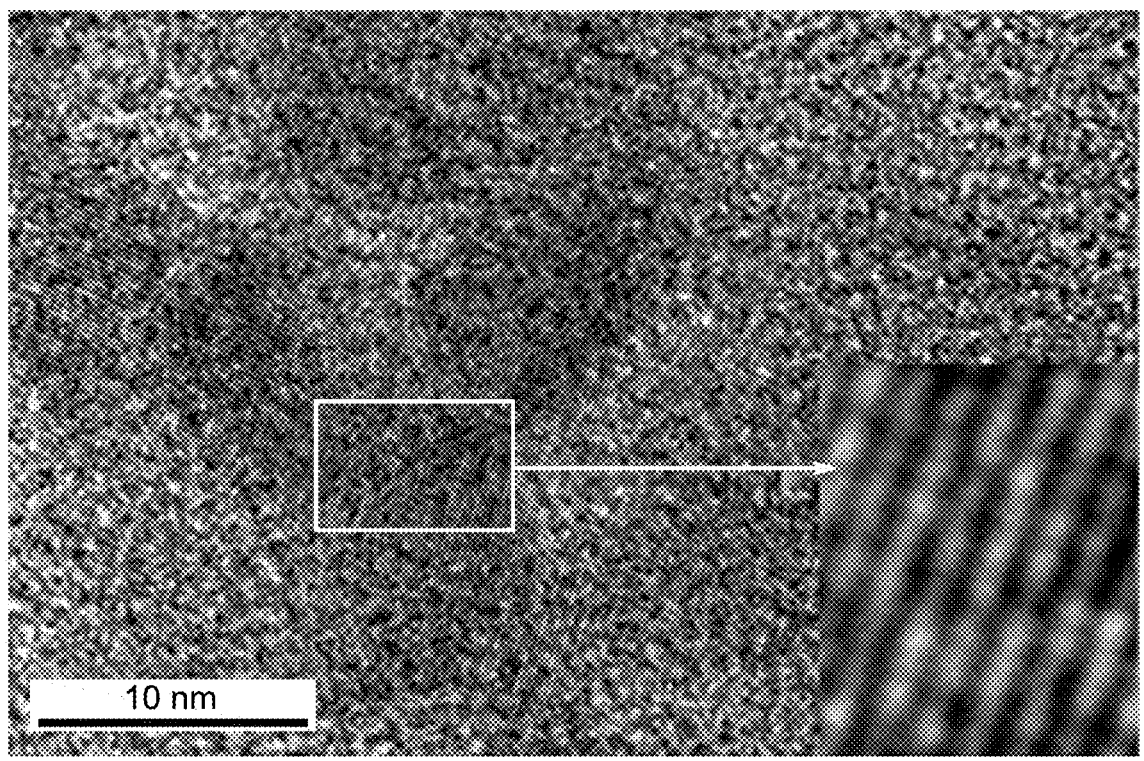
FIG. 4D is a high-resolution TEM (HR-TEM) image of COF-701 with a scale of 10 nm, according to certain embodiments.
Figure 4E:
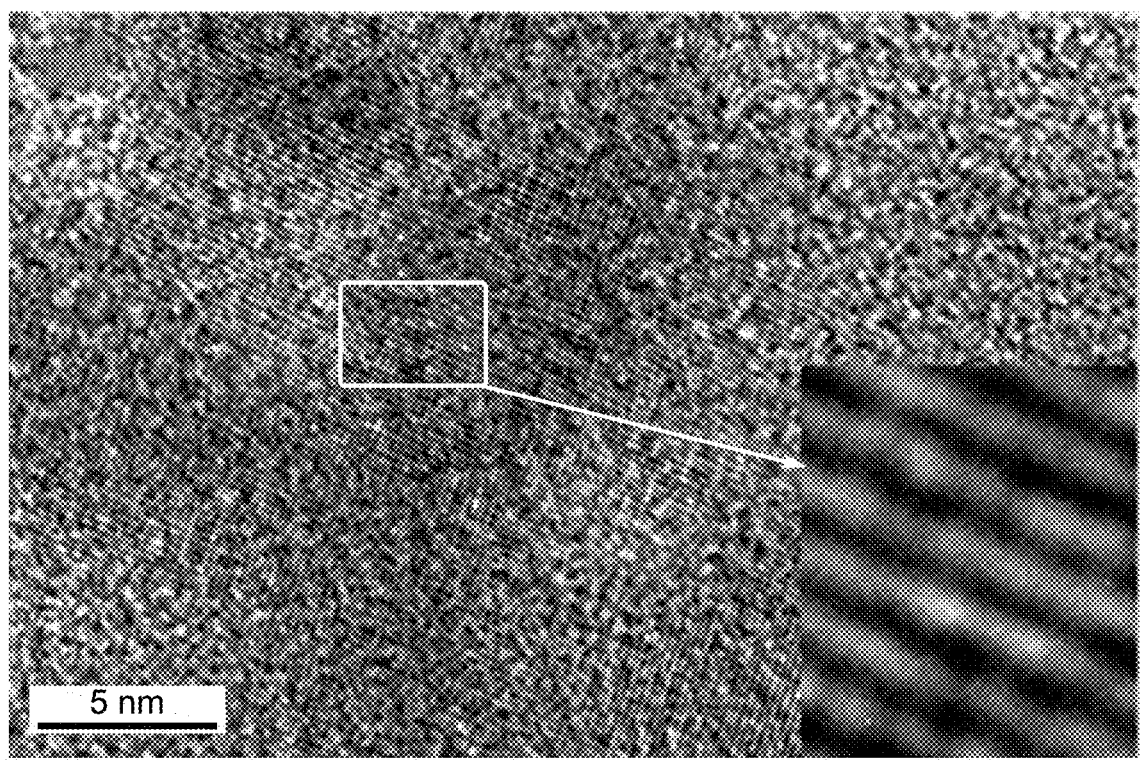
FIG. 4E is an HR-TEM image of COF-701 with a scale of 5 nm, according to certain embodiments.
Figure 4F:
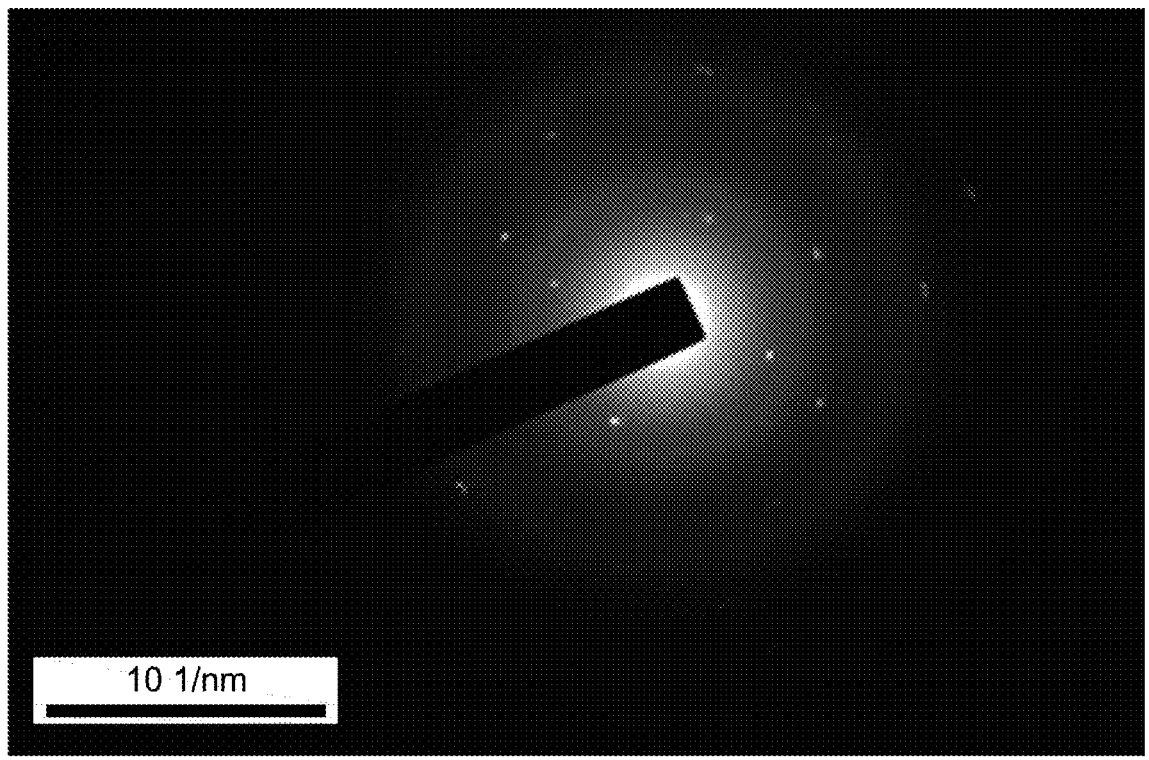
FIG. 4F is a selected area electron diffraction (SAED) pattern of COF-701, according to certain embodiments.

Orientation of lattice planes in multiple directions, as shown in FIGS. 4D-4E, substantiates the polycrystalline nature of the COF material. The diffraction patterns derived therefrom indicate a regular atomic arrangement within a densely packed crystal lattice, with an average interlayer spacing of approximately 0.2 nanometers (nm). The crystalline integrity of COF-701 is further confirmed by the selected area electron diffraction (SAED) pattern presented in FIG. 4F, which displays discrete and well-defined diffraction spots.

Figure 4G:
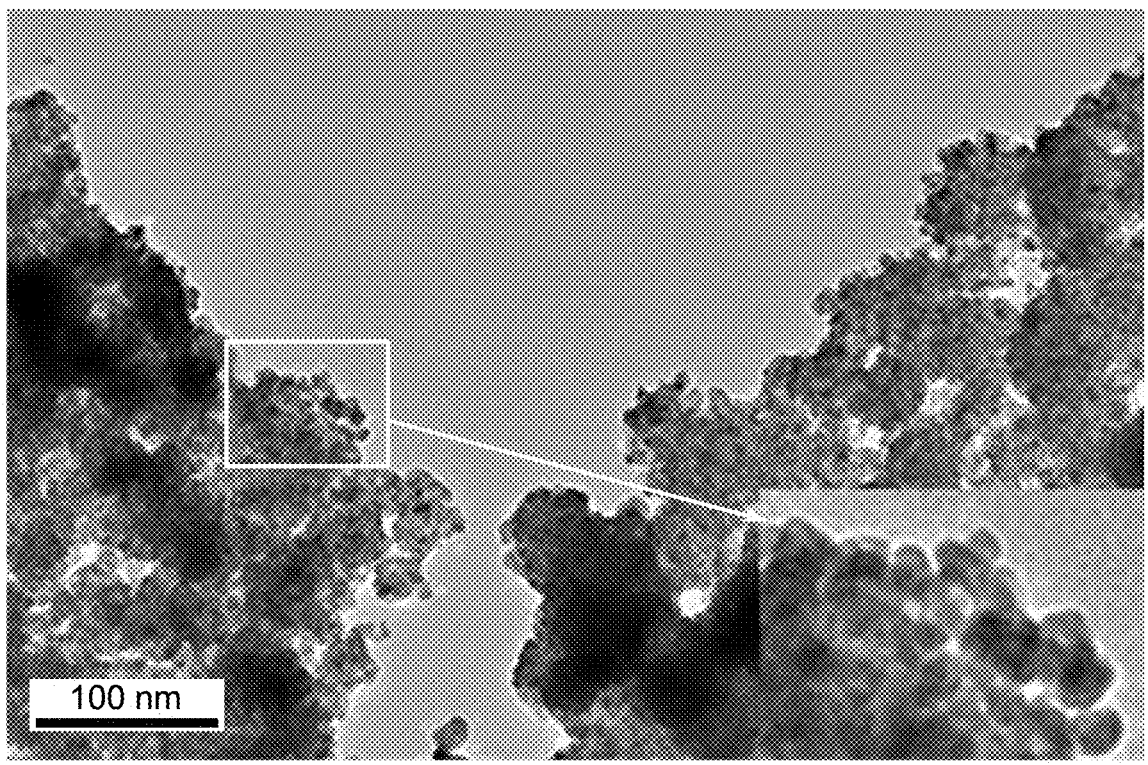
FIG. 4G is a TEM image of Pd-NP@COF-701 with a scale of 100 nm, according to certain embodiments.
Figure 4H:
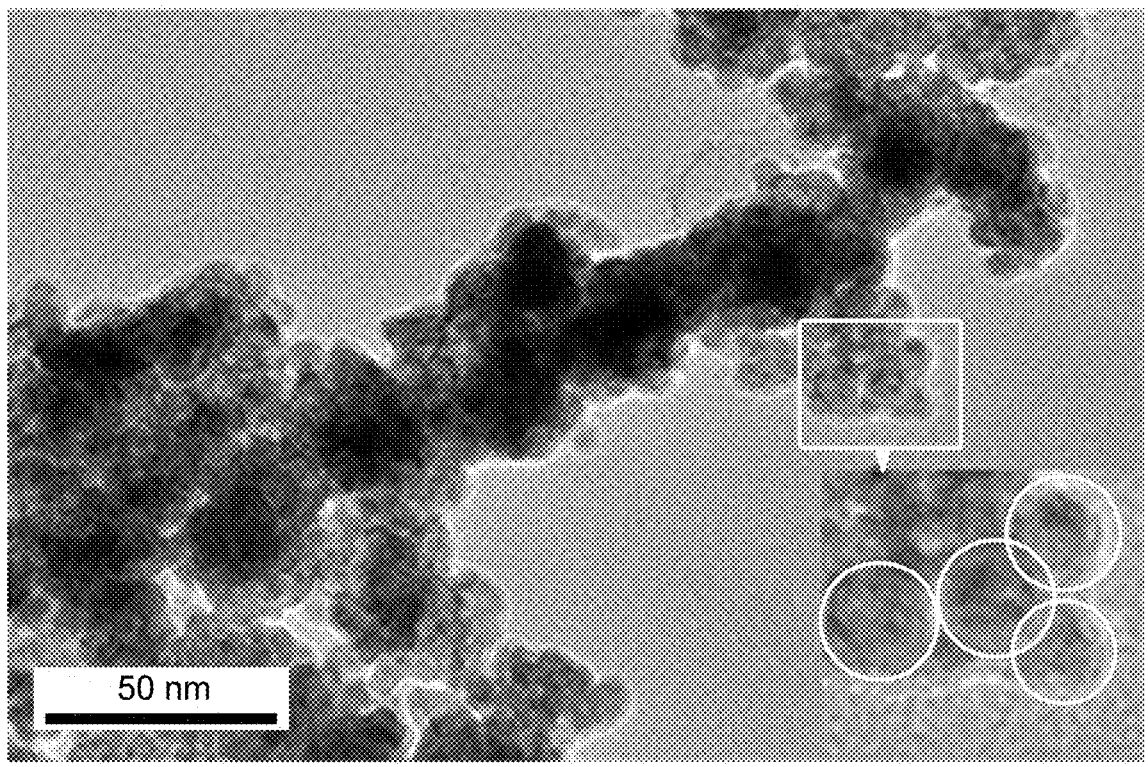
FIG. 4H is a TEM image of Pd-NP@COF-701 with a scale of 50 nm, according to certain embodiments.
Figure 4I:
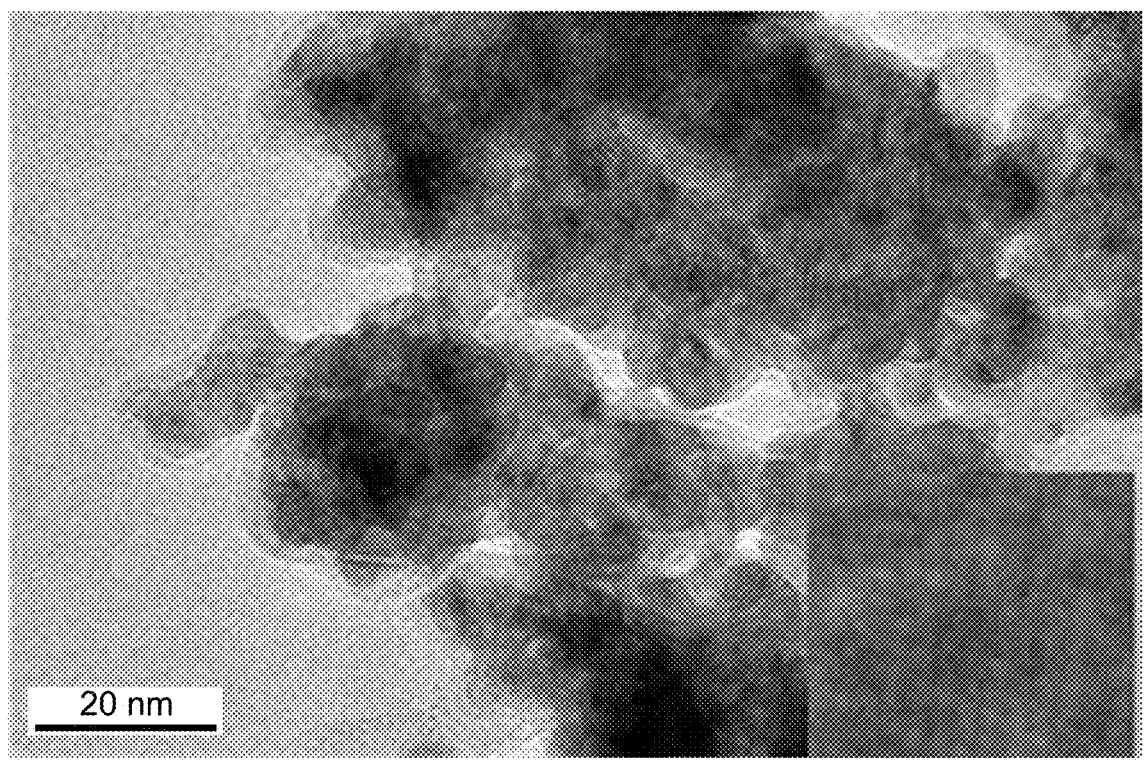
FIG. 4I is a TEM image of Pd-NP@COF-701 with a scale of 20 nm, according to certain embodiments.
Figure 4J:
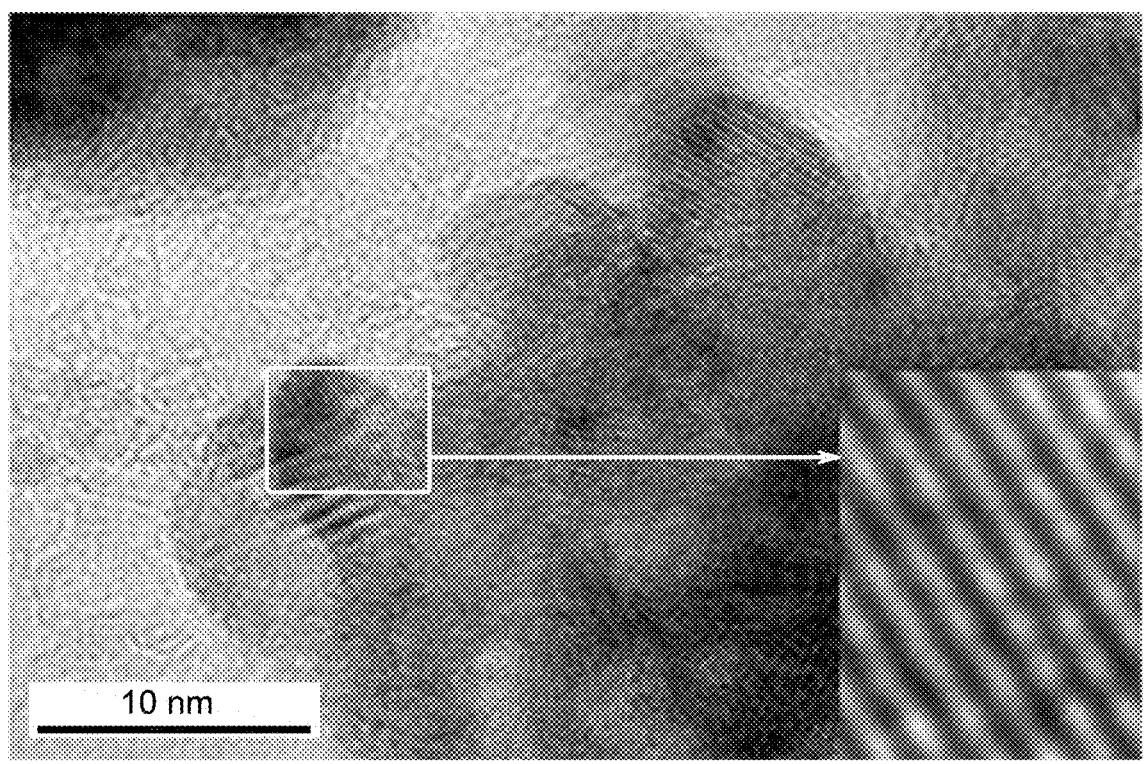
FIG. 4J is an atomic lattice fringe image of Pd-NP@COF-701 with a scale of 10 nm, according to certain embodiments.
Figure 4K:
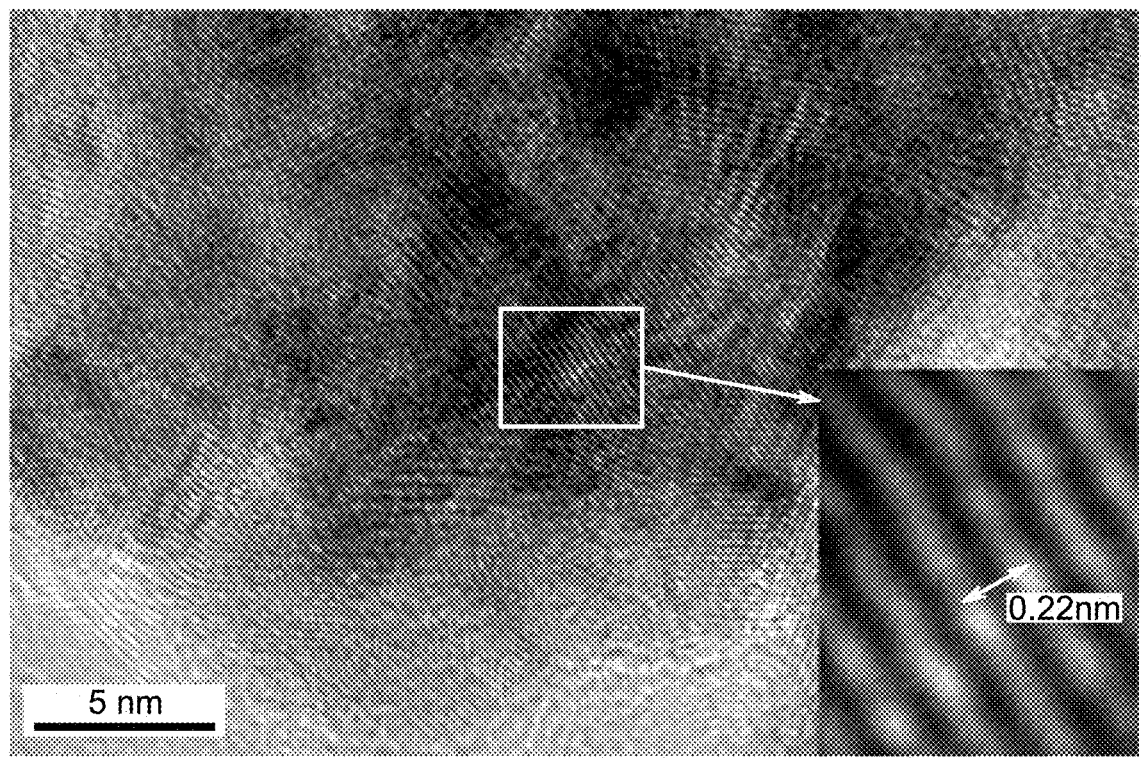
FIG. 4K is a lattice fringe image of Pd-NP@COF-701 with a scale of 5 nm, according to certain embodiments.
Figure 4L:
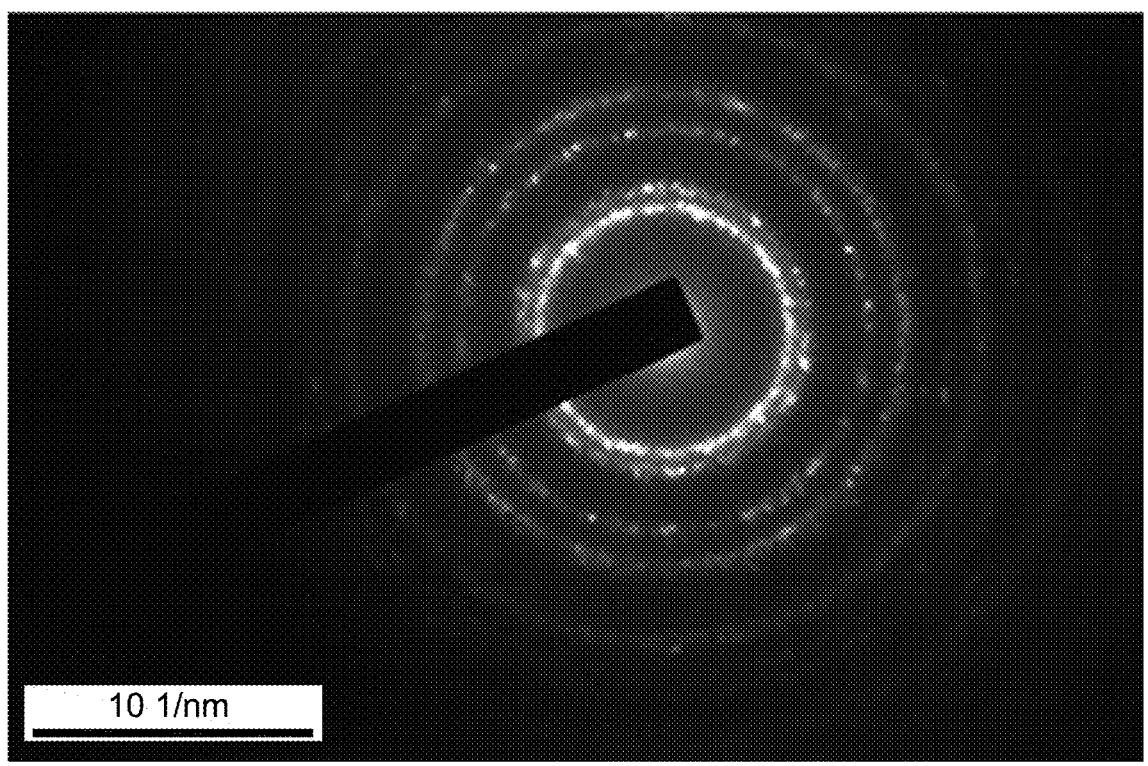
FIG. 4L is a selected area electron diffraction (SAED) image of Pd-NP@COF-701, according to certain embodiments.

Transmission electron microscopy (TEM) images of the Pd-encapsulated COF material, shown in FIGS. 4G-4I, reveal a uniform dispersion of Pd nanoparticles having sizes in the range of approximately 2 to 5 nm, as indicated by the insets of the respective figures. The atomic lattice fringes observed in the high-magnification images, as shown in FIGS. 4J-4K, exhibit an interlayer spacing of 0.22 nm, which corresponds to the lattice fringes of the face-centered cubic (FCC) structure of palladium.

Observed Pd nanoparticle sizes (2 to 5 nm) exceed the intrinsic pore width of the COF structure (1.1 nm). The nanoparticle size disparity facilitates the migration of Pd nanoparticles into the interstitial regions between COF layers, where they are subsequently stabilized through coordinate interactions with nitrogen atoms present in the triazole moiety of the COF backbone. Catalytic activity of the palladium nanoparticle-infused covalent organic framework COF-701 (Pd-NP@COF-701) was evaluated in the cycloaddition reaction of epoxides with carbon dioxide ($CO_2$) to yield cyclic carbonates. The catalytic performance was assessed under solvent-free conditions using styrene oxide (SO) as the model substrate and tetrabutylammonium salts as co-catalysts.

Control experiments were conducted to establish baseline activity. In the absence of both the Pd-NP@COF-701 catalyst and the co-catalyst, no product formation was observed. When the co-catalyst alone was employed at a reaction temperature of 100° C., a product yield of 21% was recorded, as shown in Table 1. Separately, the use of pristine palladium nitrate [$Pd(NO_3)_2$] and COF-701, each in combination with tetrabutylammonium bromide (TBABr) as a co-catalyst, resulted in 10% and 18% conversion, respectively, under identical reaction conditions of 100° C. for 12 hours, as shown in Table 1.

The Pd-NP@COF-701 catalyst used in conjunction with TBABr demonstrated enhanced performance, achieving 96% conversion at both 100° C. and 60° C. reaction temperatures, as shown in Table 1. The findings underscore the synergistic catalytic effect derived from the combination of Lewis acidic palladium nanoparticles and the COF-701 support structure, which collectively facilitate and promote the efficient transformation of epoxides into cyclic carbonates. Tetrabutylammonium iodide (TBAI) and tetrabutylammonium chloride (TBACl) were evaluated as alternative co-catalysts for catalytic efficiency of the Pd-NP@COF-701 system; however, a decrease in catalytic productivity was observed with these co-catalysts, wherein the use of TBAI and TBACl resulted in 34% and 19% conversion, respectively, as shown in Table 1.

The iodide ion ($I^-$) present in TBAI is recognized as a stronger nucleophile relative to bromide ($Br^-$) and chloride ($Cl^-$) ions, following the order of nucleophilicity: $I^->Br^->Cl^-$. The larger ionic radius of iodide compared to bromide impedes accessibility of iodide to catalytic active sites, diminishing catalytic efficiency. Bromide ions possess greater nucleophilicity and leaving group ability than chloride ions and further exhibit a more favorable size for interaction with the catalytic surface relative to iodide ions. Based on the comparative performance, tetrabutylammonium bromide (TBABr) was determined to be a more suitable co-catalyst for the cycloaddition reaction of epoxides with $CO_2$ than either TBAI or TBACl.

TABLE 1

Catalytic activity

| Entry | Catalysts | Co-catalysts | Temperature (° C.) | Yield (%) | Selectivity (%)[a] |
|---|---|---|---|---|---|
| 1 | — | — | 100 | 0 | — |
| 2 | — | TBABr | 100 | 21 | 99 |
| 3 | Pd(NO$_3$)$_2$ | TBABr | 100 | 10 | 100 |
| 4 | COF-701 | TBABr | 100 | 18 | 100 |
| 5 | Pd-NP@COF-701 | TBABr | 100 | 96 | 100 |
| 6 | Pd-NP@COF-701 | TBABr | 60 | 96 | 100 |
| 7 | Pd-NP@COF-701 | TBAI | 60 | 34 | 100 |
| 8 | Pd-NP@COF-701 | TBACl | 60 | 19 | 100 |
| 9 | Pd-NP@COF-701[b] | TBABr | 60 | 96 | 100 |

Figure 5A:
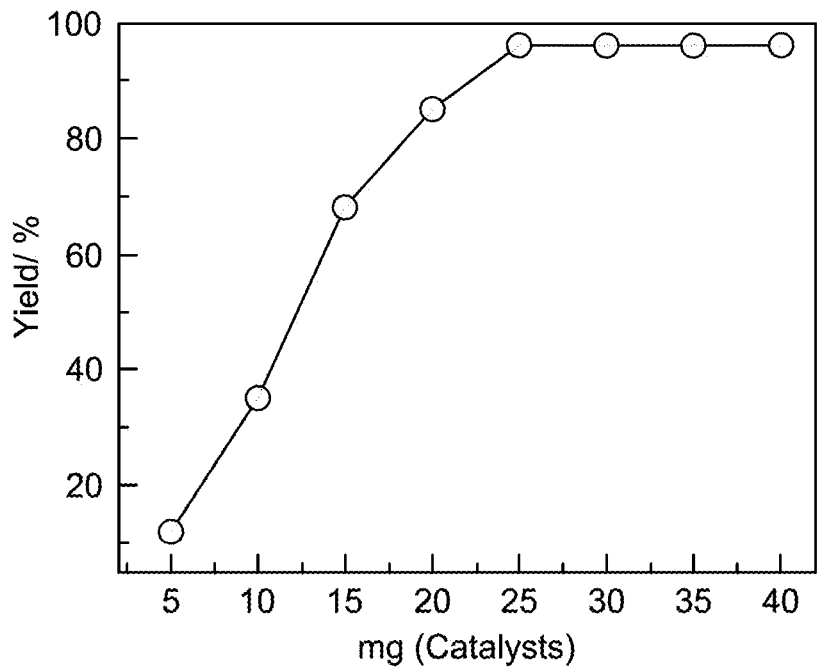
FIG. 5A illustrates the effect of varying catalyst amounts on the yield of cyclic carbonates formed using Pd-NP@COF-701 as the catalyst, according to certain embodiments.
Figure 5B:
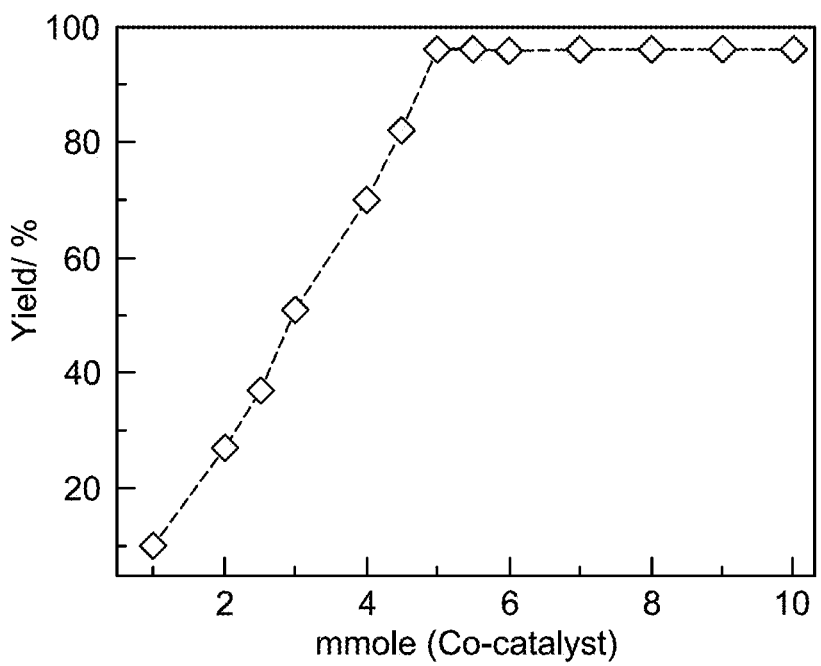
FIG. 5B illustrates the effect of different co-catalyst (TBABr) loadings on catalytic performance for cyclic carbonate formation using Pd-NP@COF-701 as the catalyst, according to certain embodiments.
Figure 5C:
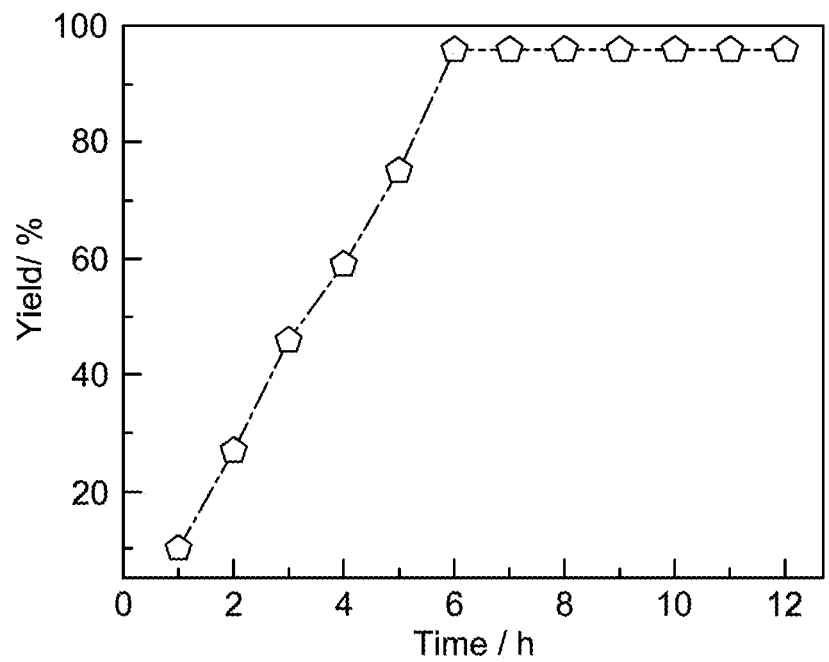
FIG. 5C illustrates the influence of reaction time on product conversion efficiency using Pd-NP@COF-701 as the catalyst, according to certain embodiments.
Figure 5D:
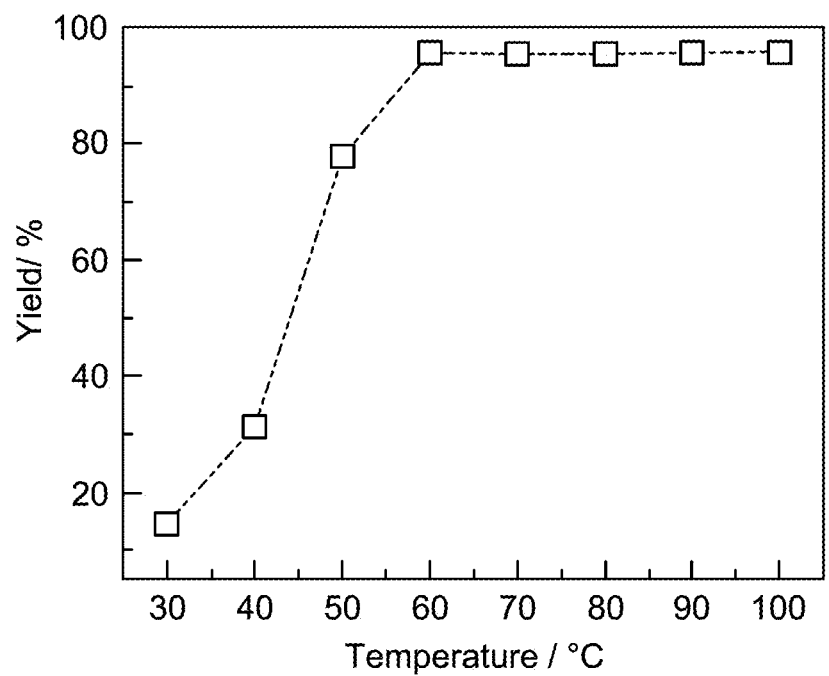
FIG. 5D illustrates the effect of reaction temperature on the yield of cyclic carbonates using Pd-NP@COF-701 as the catalyst, according to certain embodiments.
Figure 6:
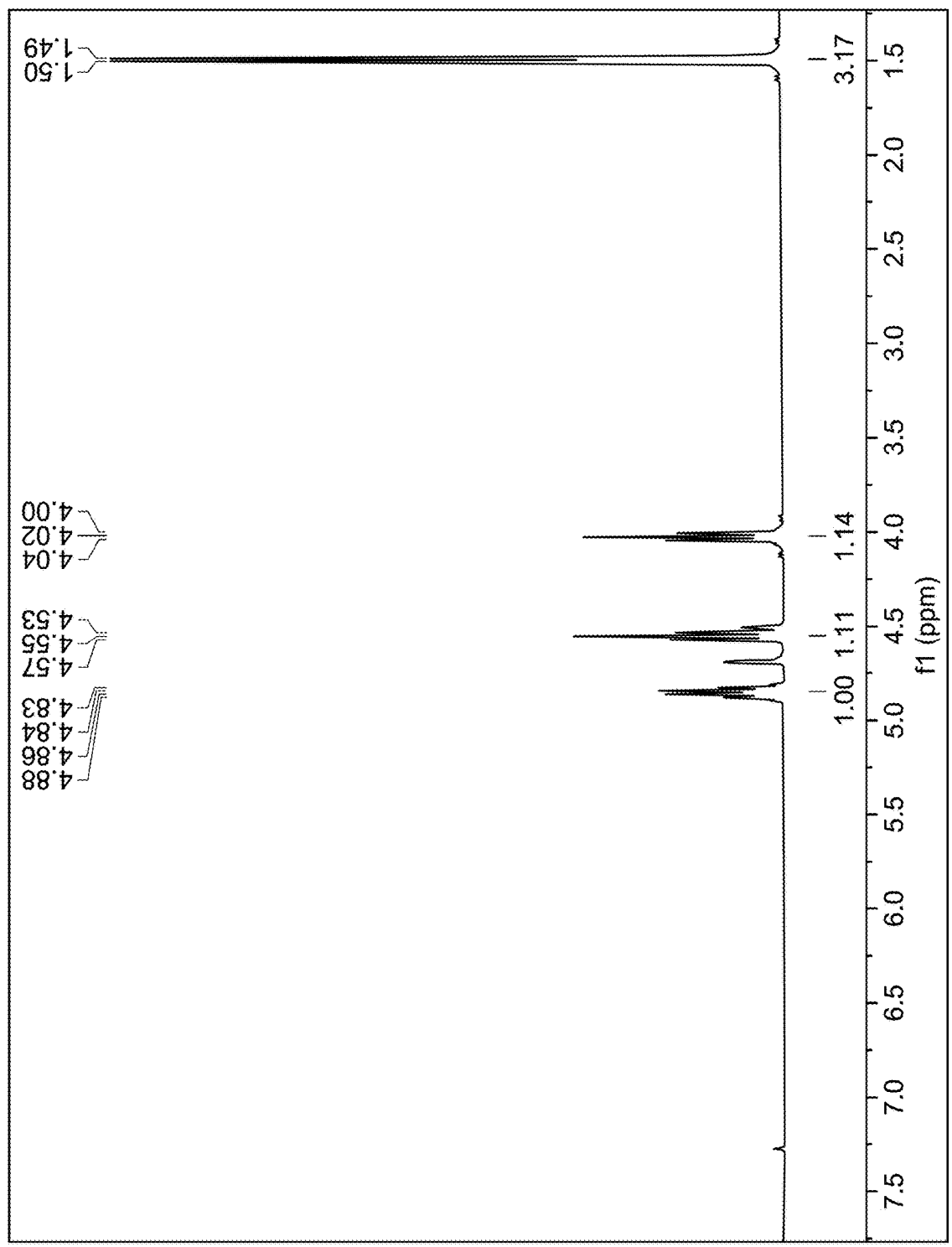
FIG. 6 is a proton nuclear magnetic resonance ($^1$H NMR) spectrum of 4-methyl-1,3-dioxolan-2-one (compound 1) recorded in $CDCl_3$ at 400 MHz, according to certain embodiments.
Figure 7:
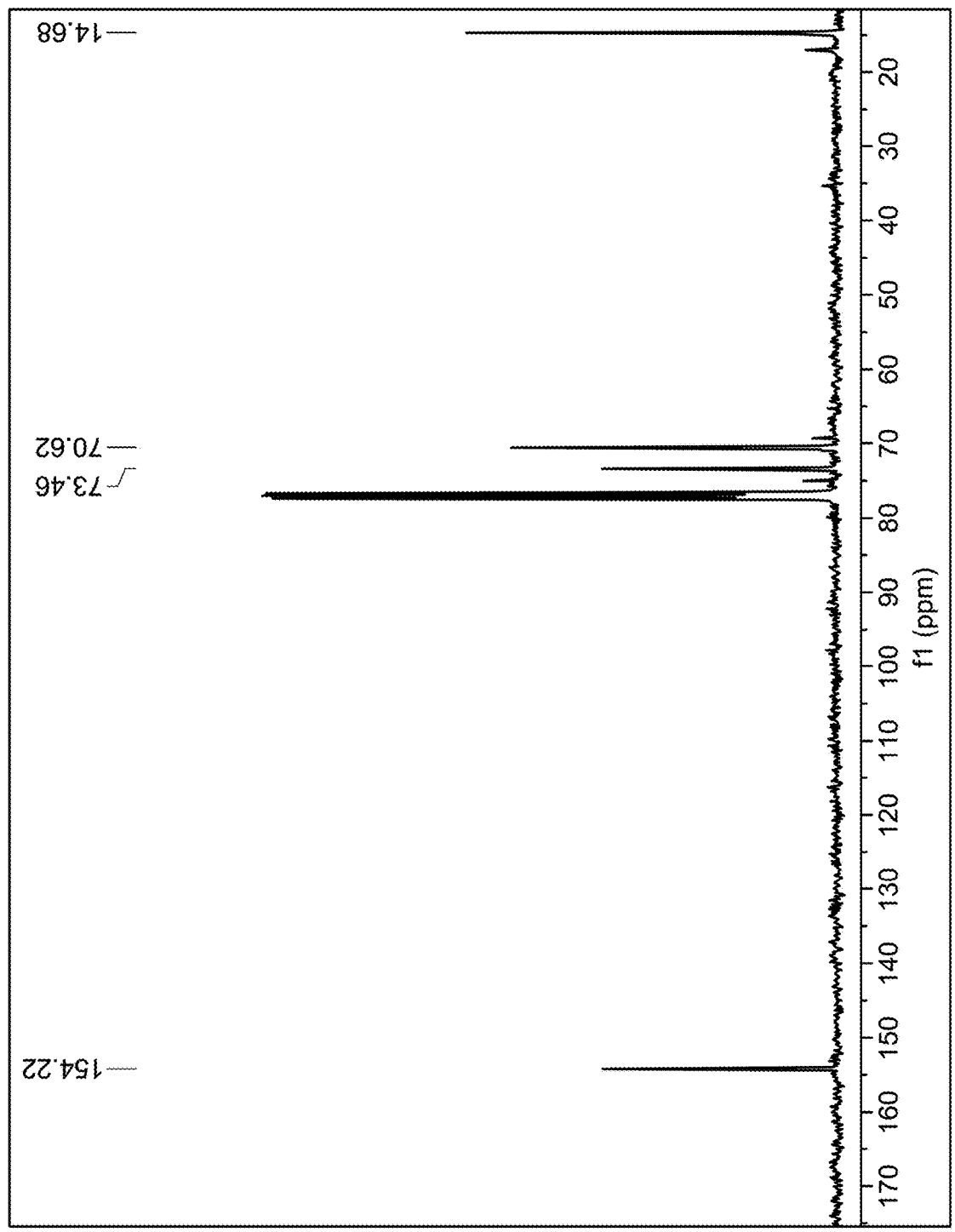
FIG. 7 is a $^{13}$C NMR spectrum of 4-methyl-1,3-dioxolan-2-one (compound 1) recorded in $CDCl_3$ at 400 MHz, according to certain embodiments.
Figure 8:
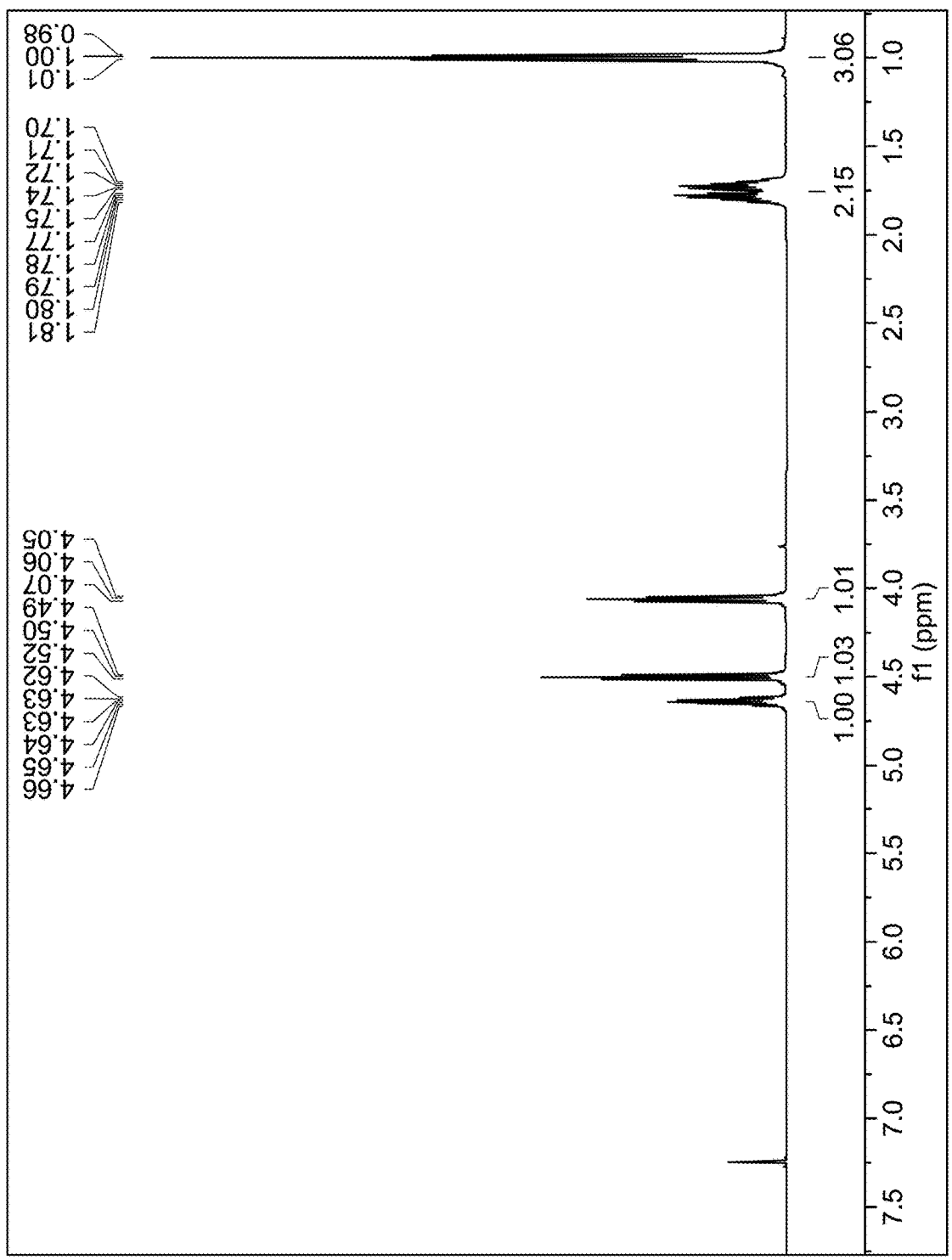
FIG. 8 is an $^1$H NMR spectrum of 4-ethyl-1,3-dioxolan-2-one (compound 2) recorded in $CDCl_3$ at 600 MHz, according to certain embodiments.
Figure 9:
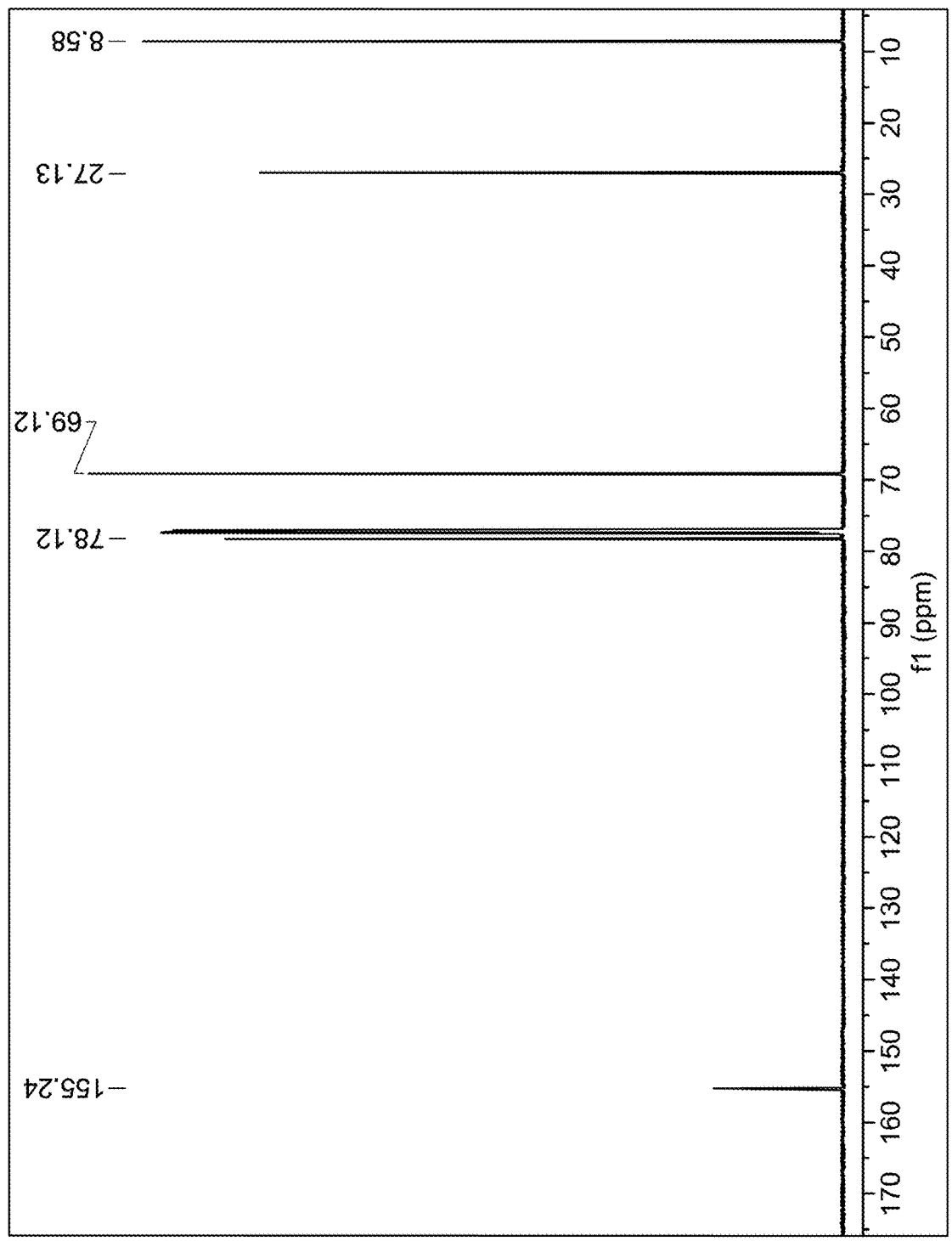
FIG. 9 is a $^{13}$C NMR spectrum of 4-ethyl-1,3-dioxolan-2-one (compound 2) recorded in $CDCl_3$ at 400 MHz, according to certain embodiments.
Figure 10:
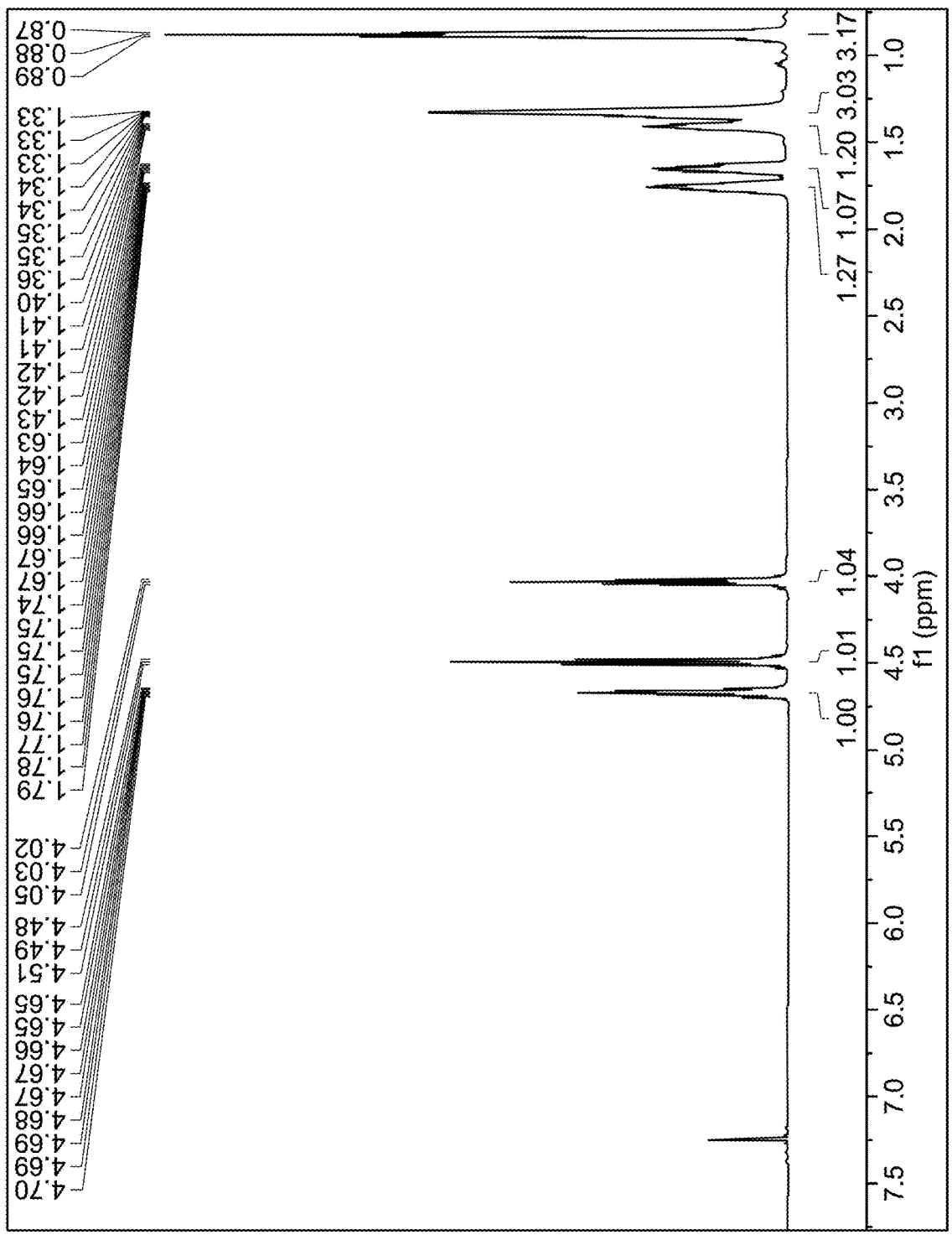
FIG. 10 is an $^1$H NMR spectrum of 4-butyl-1,3-dioxolan-2-one (compound 3) recorded in $CDCl_3$ at 600 MHz, according to certain embodiments.
Figure 11:
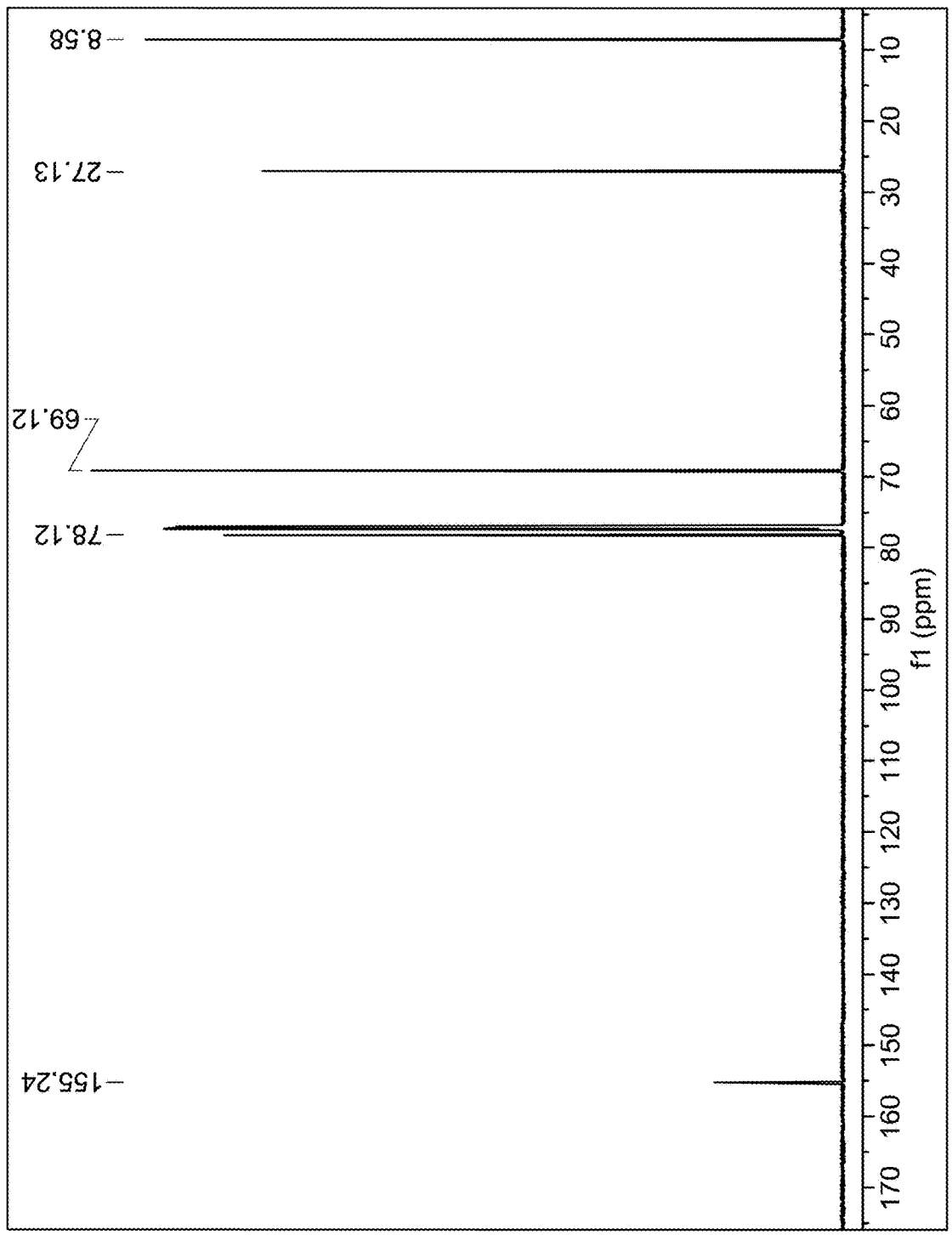
FIG. 11 is a $^{13}$C NMR spectrum of 4-butyl-1,3-dioxolan-2-one (compound 3) recorded in $CDCl_3$ at 400 MHz, according to certain embodiments.
Figure 12:
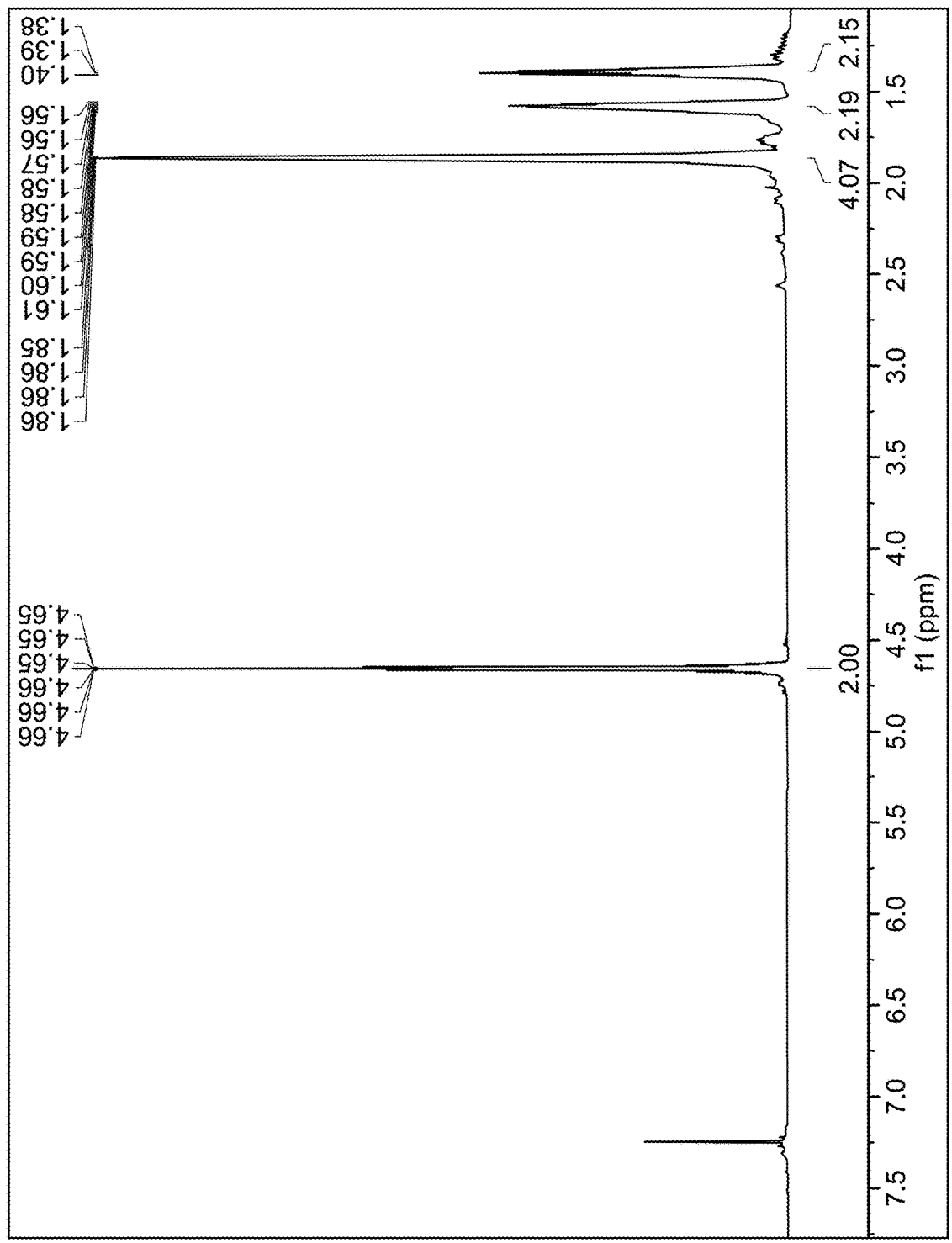
FIG. 12 is an $^1$H NMR spectrum of hexahydrobenzo[d][1,3]dioxol-2-one (compound 4) recorded in $CDCl_3$ at 600 MHz, according to certain embodiments.
Figure 13:
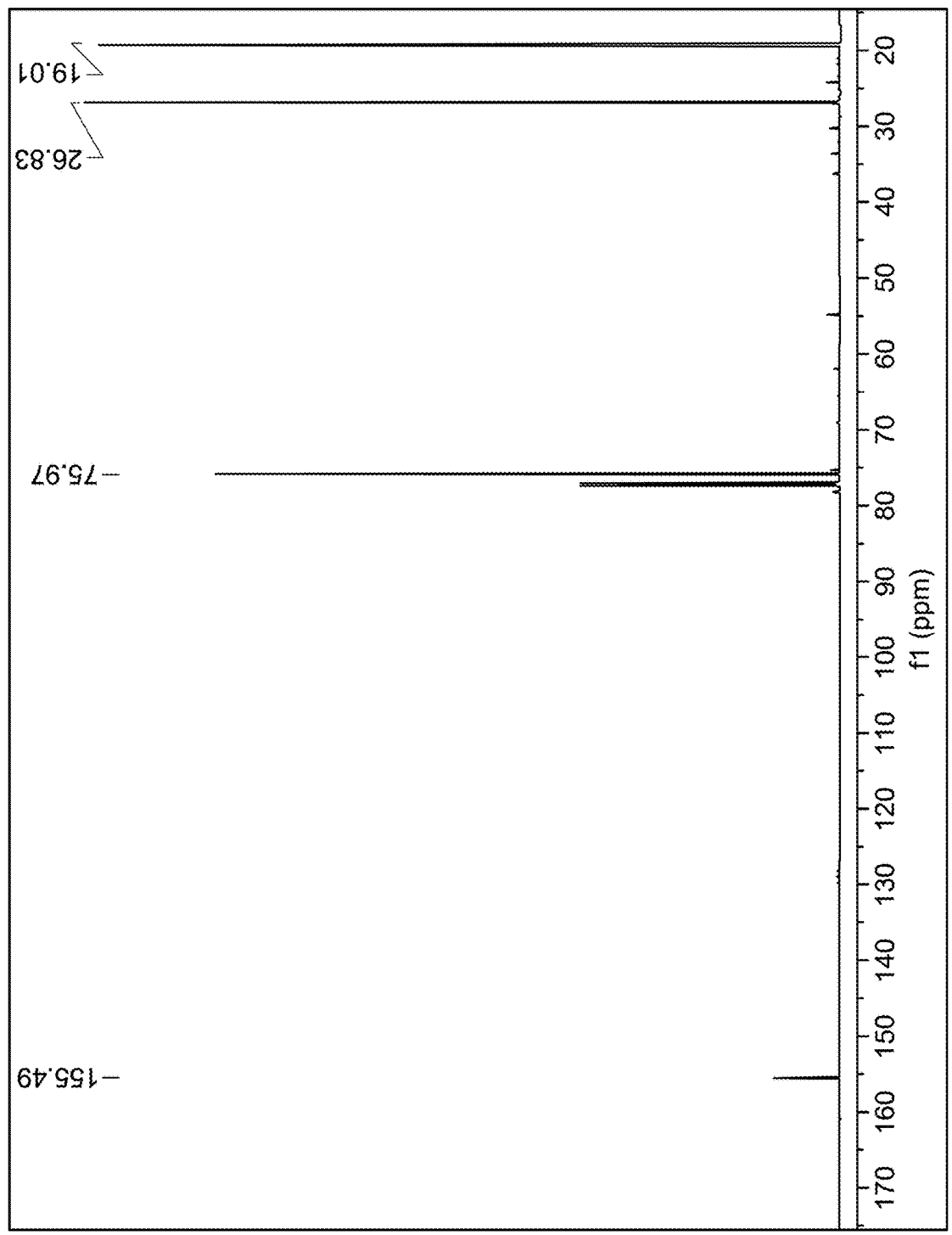
FIG. 13 is a $^{13}$C NMR spectrum of hexahydrobenzo[d][1,3]dioxol-2-one (compound 4) recorded in $CDCl_3$ at 400 MHz, according to certain embodiments.
Figure 14:
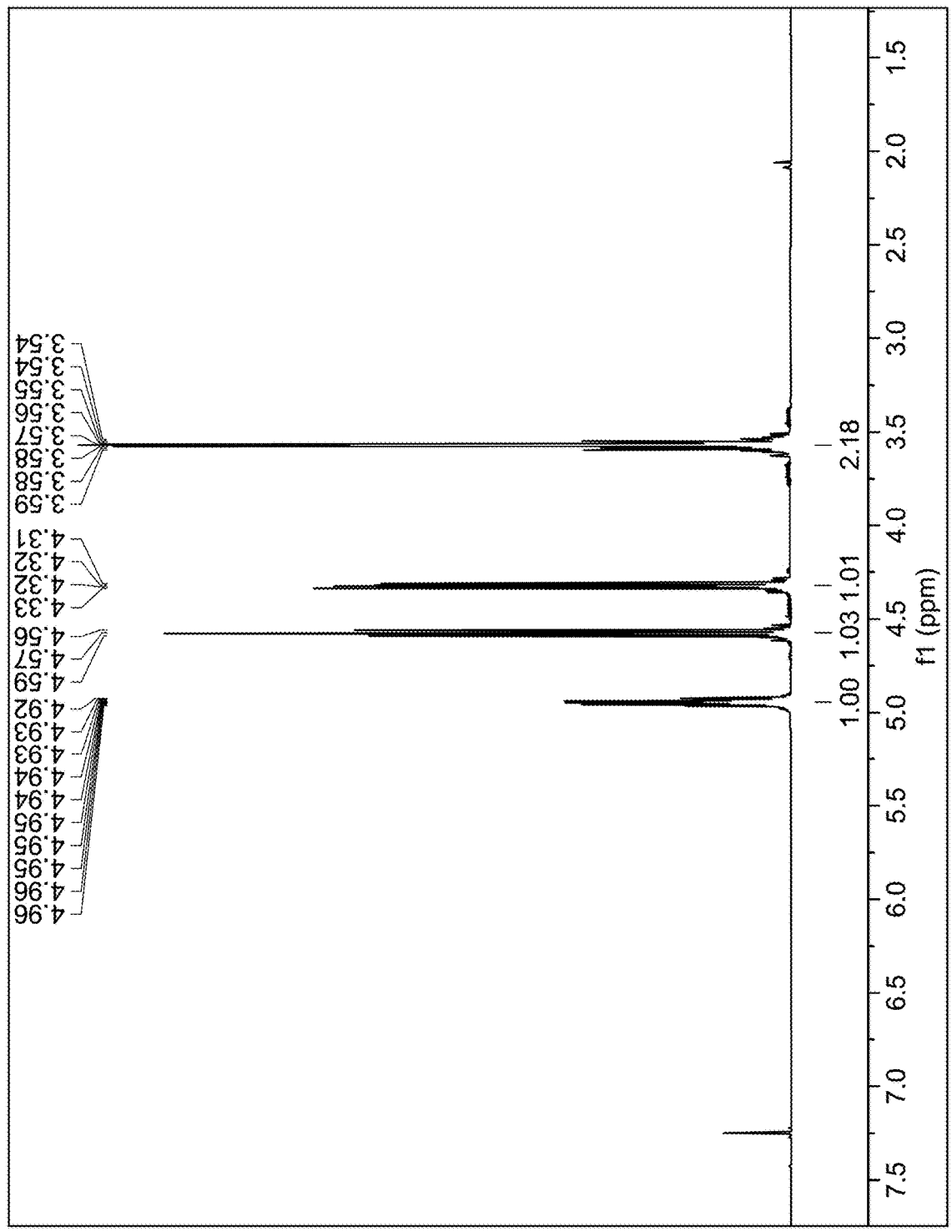
FIG. 14 is an $^1$H NMR spectrum of 4-(chloromethyl)-1,3-dioxolan-2-one (compound 5) recorded in $CDCl_3$ at 600 MHz, according to certain embodiments.
Figure 15:
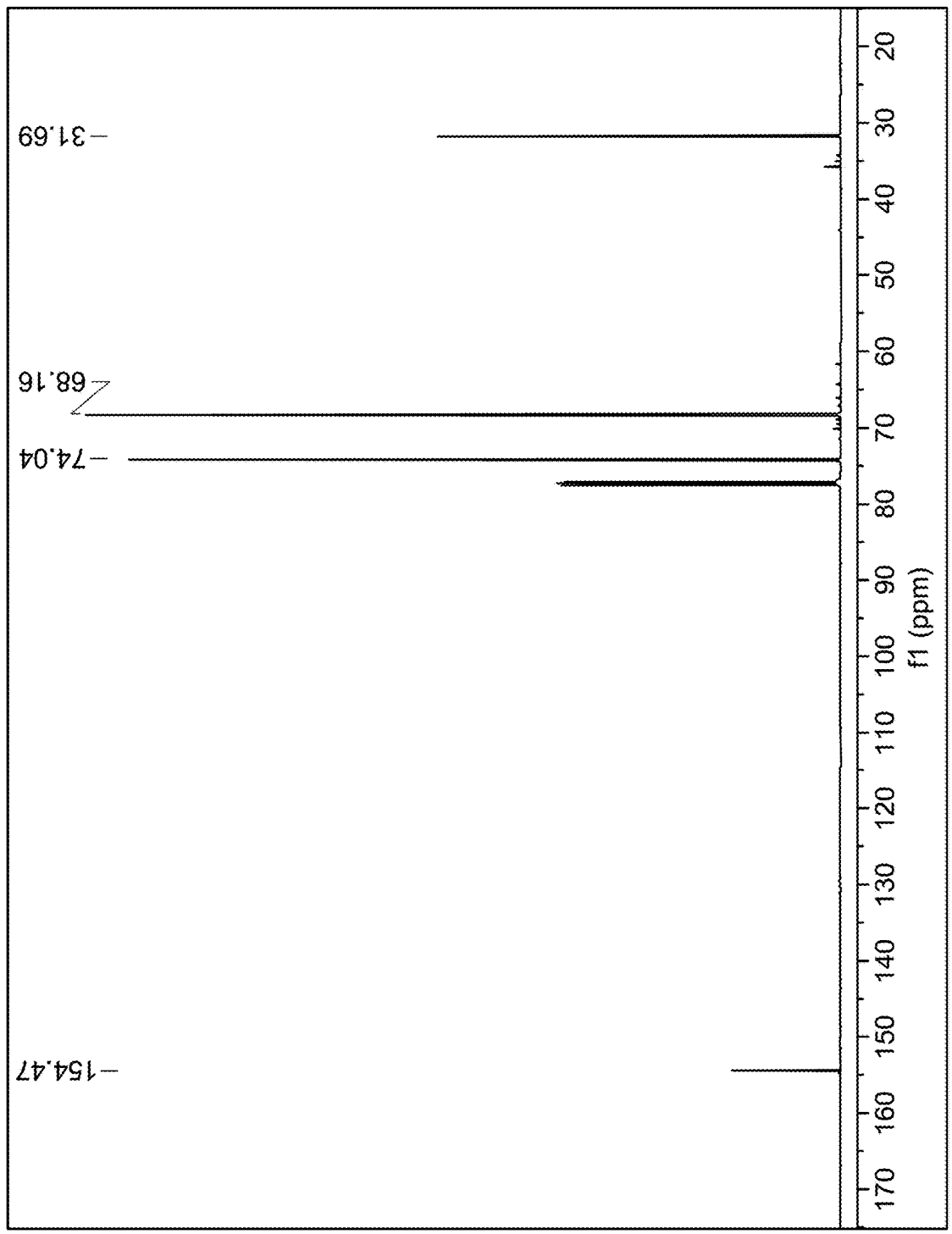
FIG. 15 is a $^{13}$C NMR spectrum of 4-(chloromethyl)-1,3-dioxolan-2-one (compound 5) recorded in $CDCl_3$ at 400 MHz, according to certain embodiments.
Figure 16:
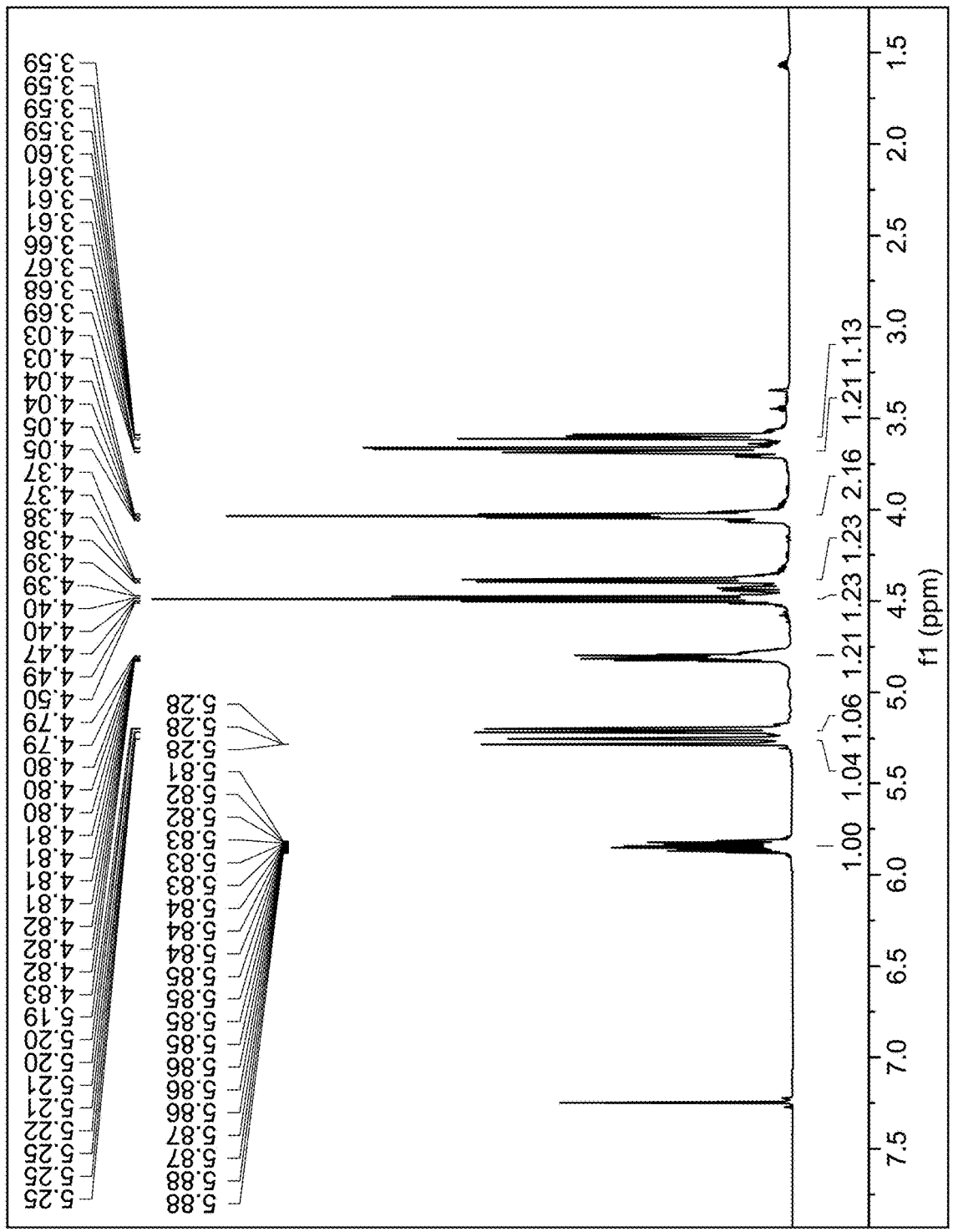
FIG. 16 is an $^1$H NMR spectrum of 4-(allyloxy)-1,3-dioxolan-2-one (compound 6) recorded in $CDCl_3$ at 600 MHz, according to certain embodiments.
Figure 17:
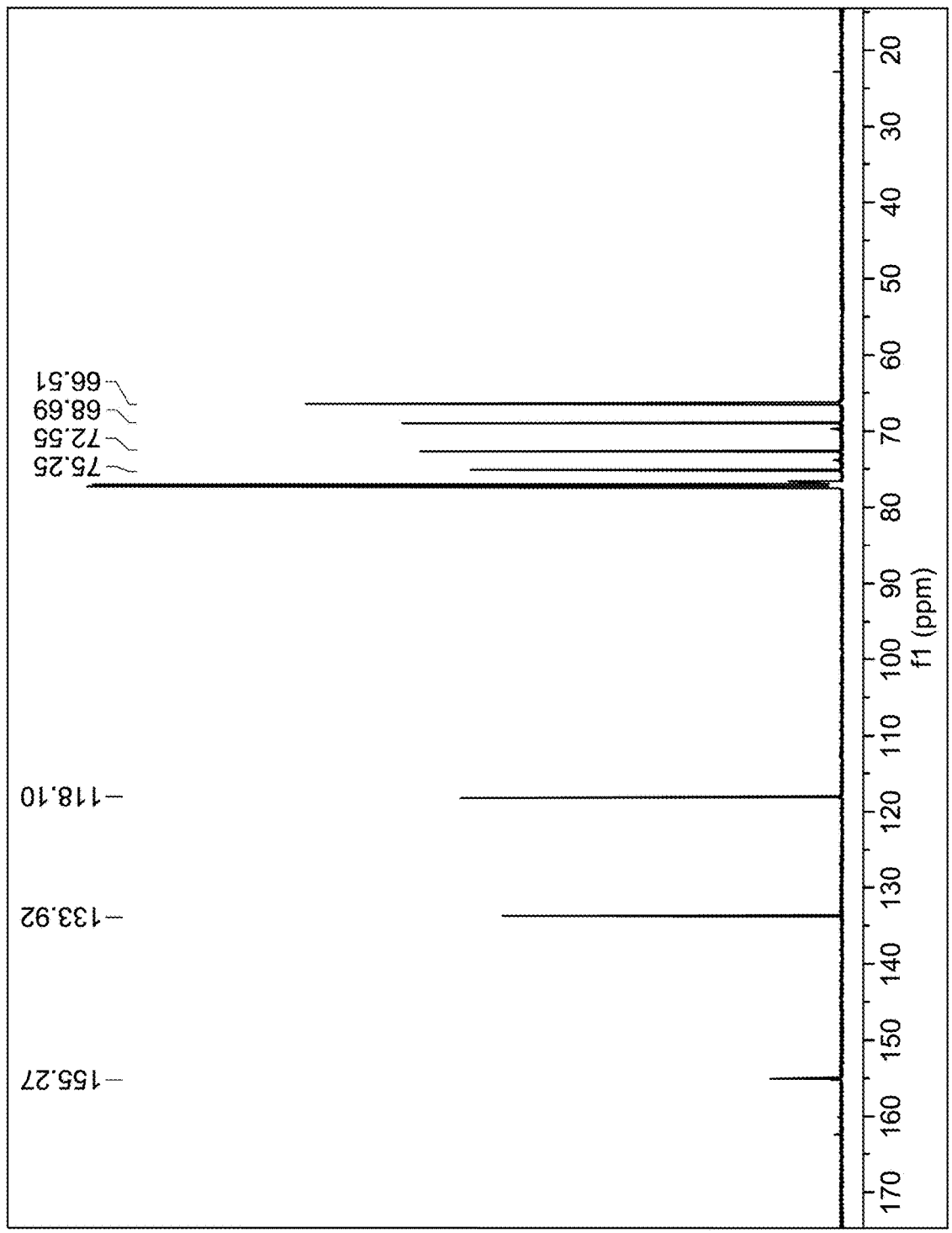
FIG. 17 is a $^{13}$C NMR spectrum of 4-(allyloxy)-1,3-dioxolan-2-one (compound 6) recorded in $CDCl_3$ at 400 MHz, according to certain embodiments.
Figure 18:
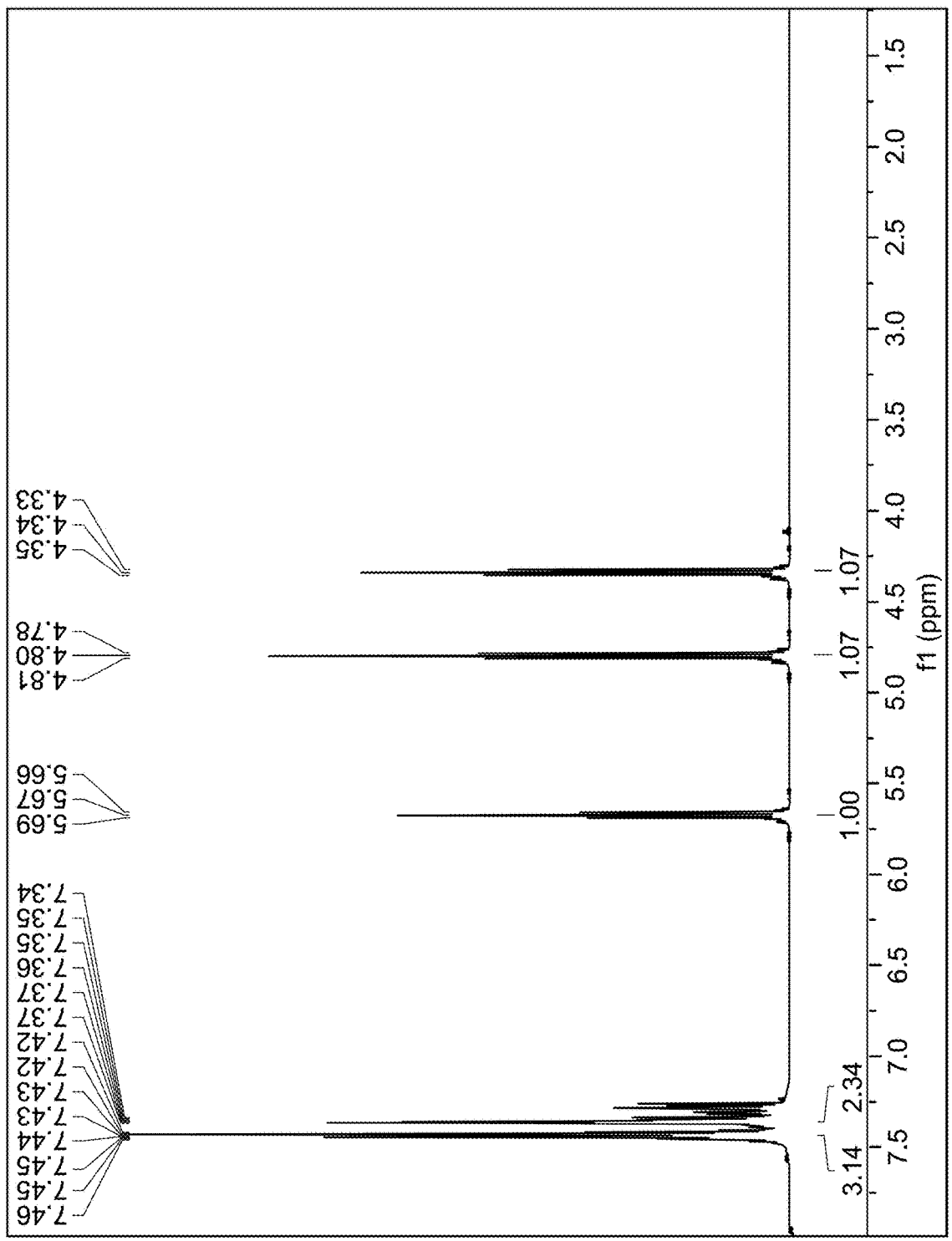
FIG. 18 is an $^1$H NMR spectrum of 4-phenyl-1,3-dioxolan-2-one (compound 7) recorded in $CDCl_3$ at 600 MHz, according to certain embodiments.
Figure 19:
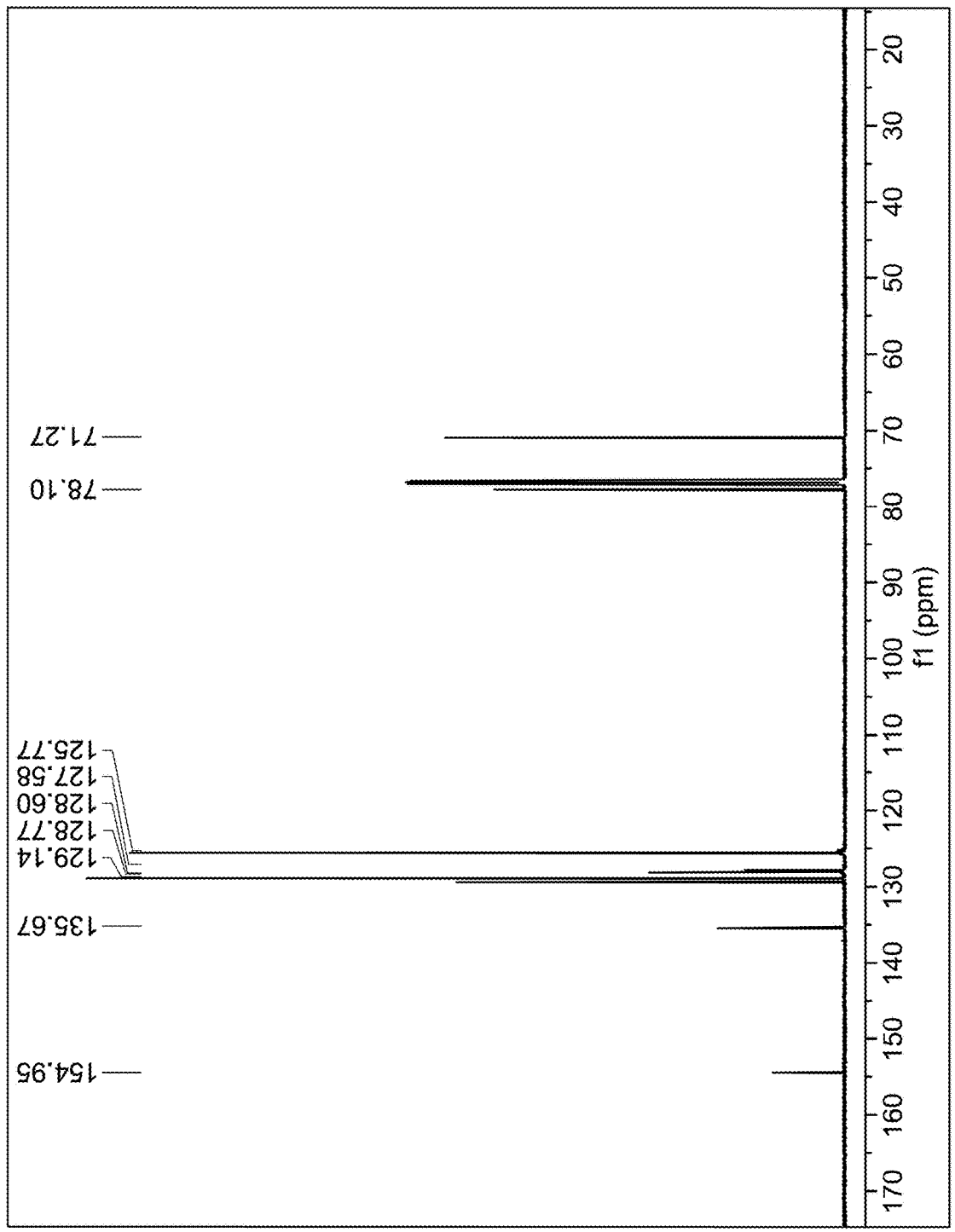
FIG. 19 is a $^{13}$C NMR spectrum of 4-phenyl-1,3-dioxolan-2-one (compound 7) recorded in $CDCl_3$ at 400 MHz, according to certain embodiments.
Figure 20:
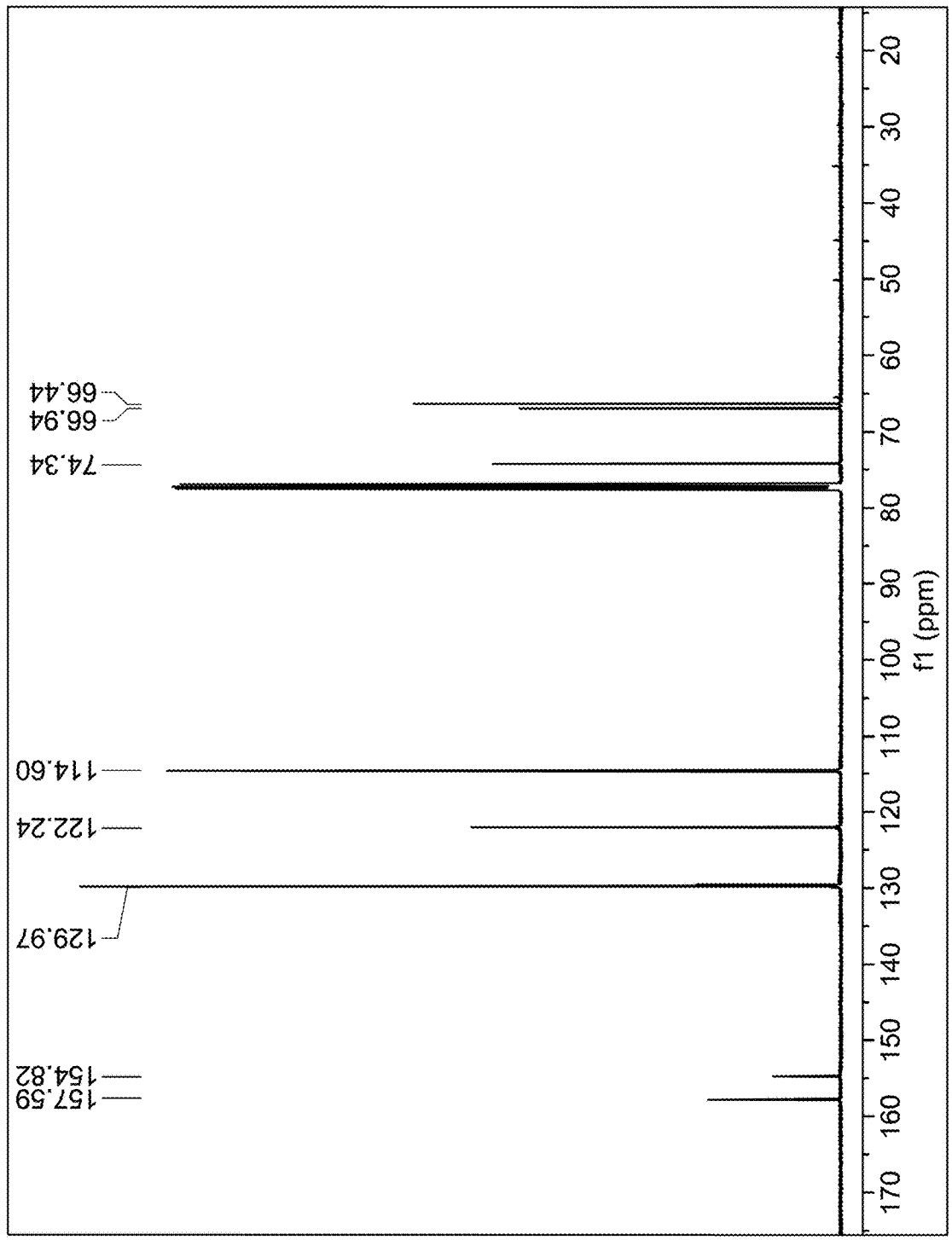
FIG. 20 is an $^1$H NMR spectrum of 4-(phenoxymethyl)-1,3-dioxolan-2-one (compound 8) recorded in $CDCl_3$ at 600 MHz, according to certain embodiments.

Reaction conditions: styrene oxide (10 mmol), catalysts (25 mg), co-catalyst (5 mmol), 12 hours
[a]Selectivity was based on $^1$H NMR spectra of the crude reaction mixtures
[b]6-hour reaction time Reaction conditions: styrene oxide (10 mmol), catalysts (25 mg), co-catalyst (5 mmol), 12 hours
[a]Selectivity was based on $^1$H NMR spectra of the crude reaction mixtures
[b]6-hour reaction time Cycloaddition reaction conditions for the conversion of styrene oxide (SO) and carbon dioxide (CO$_2$) to cyclic carbonates were determined. Influence of reaction parameters including catalyst loading, co-catalyst loading, reaction time, and temperature was examined to determine conditions that yield maximum product conversion. Results are depicted in FIGS. 5A-5D, where FIGS. 5A-5B illustrate the effect of catalyst and co-catalyst loading, FIG. 5C represents the influence of reaction time, and FIG. 5D shows the variation in catalytic performance with respect to temperature. Conversion of styrene oxide to the corresponding cyclic carbonate was achieved using a catalyst loading of 25 mg, a co-catalyst loading of 5.0 mmol of tetrabutylammonium bromide (TBABr), a reaction temperature of 60° C., and a reaction duration of 6 hours.

To evaluate a versatility of the Pd-NP@COF-701 catalytic system, a range of aliphatic and aromatic epoxide substrates were subjected to cycloaddition with CO$_2$ under a catalyst loading of 25 mg, a co-catalyst loading of 5.0 mmol of tetrabutylammonium bromide (TBABr), a reaction temperature of 60° C., and a reaction duration of 6 hours. The results are summarized in Table 2, which demonstrates that the catalyst facilitates the conversion of the epoxides to their respective cyclic carbonates at 60° C., with TBABr as the co-catalyst, and within a 6-hour reaction period. Reported yields range from 88 to 96%. The porous architecture and large surface area of COF-701 enables facile diffusion of reactants and accessibility to the Lewis acidic active sites. Specifically, the framework permits unhindered penetration of small, linear aliphatic epoxides such as 1,2-epoxypropane, 1,2-epoxybutane, 1,2-epoxyhexane, allyl glycidyl ether, and epichlorohydrin as well as bulkier aromatic epoxides, including styrene oxide and phenylglycidyl ether, as shown in Table 2. A reduction in yield was observed for cyclohexene oxide, which possesses a sterically hindered disubstituted ring structure that limits its access to the catalytic sites.

TABLE 2

Synthesis of Cyclic Carbonates from Various Epoxides

| Entry | R | Products | Yield[a] (%) |
|---|---|---|---|
| 1 | —CH$_3$ | | 88 |
| 2 | —CH$_2$CH$_3$ | | 95 |
| 3 | —CH$_2$CH$_2$CH$_2$CH$_3$ | | 97 |
| 4 | (cyclohexene oxide) | | 43 |
| 5 | —CH$_2$Cl | | 95 |

TABLE 2-continued

Synthesis of Cyclic Carbonates from Various Epoxides

| Entry | R | Products | Yield[a] (%) |
|---|---|---|---|
| 6 | (allyloxymethyl) | (4-(allyloxymethyl)-1,3-dioxolan-2-one) | 90 |
| 7 | (phenyl) | (4-phenyl-1,3-dioxolan-2-one) | 96 |
| 8 | (phenoxymethyl) | (4-(phenoxymethyl)-1,3-dioxolan-2-one) | 94 |

Reaction conditions: substrate (10 mmol), catalysts (25 mg), co-catalyst (5 mmol), 6-hour reaction time, temperature (60° C.)
[a]Yield was determined from $^1$H NMR spectra Reaction conditions: substrate (10 mmol), catalysts (25 mg), co-catalyst (5 mmol), 6-hour reaction time, temperature (60° C.)

[a]Yield was determined from $^1$H NMR spectra

The yield and selectivity of the resulting cyclic carbonates for each substrate were confirmed through spectroscopic analysis of the isolated products using $^1$H NMR and carbon-13 nuclear magnetic resonance ($^{13}$C NMR) spectroscopy, as described in hereinafter.

$^1$HNMR and $^{13}$CNMR of the $CO_2$ Cycloaddition Products:

4-Methyl-1,3-dioxolan-2-one (Compound 1)

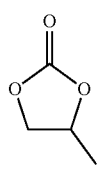

$^1$H NMR (CDCl$_3$, 400 MHz, ppm.): δ 4.85 (q, J=6.7 Hz, 1H), 4.55 (t, J=8.0 Hz, 1H), 4.02 (t, J=8.0 Hz, 1H), 1.50 (d, J=4.0 Hz, 3H); $^{13}$C NMR (CDCl$_3$, 400 MHz, ppm): δ 154.22, 73.46, 70.62, 14.68.

4-Ethyl-1,3-dioxolan-2-one (Compound 2)

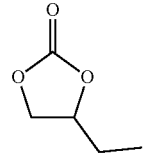

$^1$H NMR (CDCl$_3$, 600 MHz, ppm.): δ 4.66-4.62 (m, 1H), 4.50 (t, J=6.0 Hz, 1H), 4.06 (t, J=6.0 Hz, 1H), 1.81-1.70 (m, 2H), 1.00 (t, J=9.00 Hz, 3H); $^{13}$C NMR (CDCl$_3$, 400 MHz, ppm): δ 155.24, 78.12, 69.12, 27.13, 8.58.

4-Butyl-1,3-dioxolan-2-one (Compound 3)

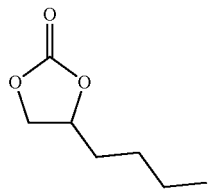

$^1$H NMR (CDCl$_3$, 600 MHz, ppm.): δ 4.70-4.65 (m, 1H), 4.49 (t, J=9.0 Hz, 1H), 4.03 (t, J=9.0 Hz, 1H), 1.79-1.63 (m, 2H), 1.43-1.33 (m, 4H), 0.88 (t, J=6.0 Hz, 3H); $^{13}$C NMR (CDCl$_3$, 400 MHz, ppm): δ 155.25, 76.96, 69.39, 33.73, 26.38, 22.43, 13.75.

Hexahydrobenzo[d][1,3]dioxol-2-one (Compound 4)

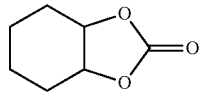

$^1$H NMR (CDCl$_3$, 600 MHz, ppm.): δ 4.65 (t, J=3.0 Hz, 2H), 1.85 (d, J=6.0 Hz, 4H), 1.61-1.56 (m, 2H), 1.40-1.38 (m, 2H); $^{13}$C NMR (CDCl$_3$, 400 MHz, ppm): δ 155.49, 75.97, 26.83, 19.01.

4-(Chloromethyl)-1,3-dioxolan-2-one (Compound 5)

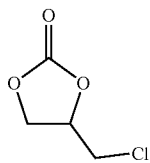

$^1$H NMR (CDCl$_3$, 600 MHz, ppm): δ 4.96-4.92 (m, 1H), 4.57 (t, J=9.0 Hz, 1H), 4.32 (t, J=6.0 Hz, 1H), 3.59-3.54 (m, 2H); $^{13}$C NMR (CDCl$_3$, 400 MHz, ppm): δ 154.47, 74.04, 68.16, 31.69.

4-(Allyloxy)-1,3-dioxolan-2-one (Compound 6)

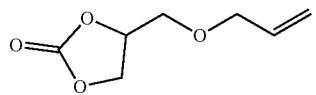

$^1$H NMR (600 MHz, ppm, CDCl$_3$) δ 5.88-5.81 (m, 1H), 5.26 (dt, J=9.0, 1.31 Hz, 1H), 5.21 (dt, J=6.0, 1.90 Hz, 1H), 4.83-4.79 (m, 1H), 4.49 (t, J=9.0 Hz, 1H), 4.38 (t, J=6.6 Hz, 1H), 4.04 (t, J=5.5 Hz, 2H), 3.69-3.66 (dd, J=12.0, 6.0 Hz, 1H), 3.61-3.59 (dd, J=12.0, 6.0 Hz, 1H). $^{13}$C NMR (400 MHz, ppm, CDCl$_3$) δ 155.27, 133.92, 118.10, 75.25, 72.55, 68.91, 66.51.

4-Phenyl-1,3-dioxolan-2-one (Compound 7)

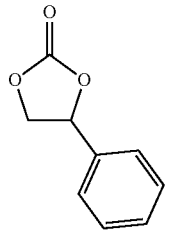 [SMILES: O=C1OCC(c2ccccc2)O1]

$^1$H NMR (CDCl$_3$, 600 MHz, ppm.): δ 7.46-7.34 (m, 5H), 5.67 (t, J=9.0 Hz, 1H), 4.80 (t, J=9.0 Hz, 1H), 4.34 (t, J=9.0 Hz, 1H); $^{13}$C NMR (CDCl$_3$, 400 MHz, ppm): δ 154.95, 135.67, 129.14, 128.60, 125.77, 78.10, 71.27.

4-(phenoxymethyl)-1,3-dioxolan-2-one (Compound 8)

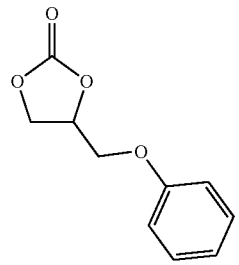 [SMILES: O=C1OCC(COc2ccccc2)O1]

$^1$H NMR (CDCl$_3$, 600 MHz, ppm.): δ 7.31 (t, J=9.0 Hz, 2H), 7.02 (t, J=9.0 Hz, 1H), 6.91 (d, J=7.8 Hz, 2H), 5.04-5.01 (m, 1H), 4.61 (t, J=8.4 Hz, 1H), 4.53 (t, J=6.0 Hz, 1H), 4.25-4.22 (dd, J=10.4, 4.1 Hz, 1H), 4.15-4.12 (dd, J=10.8, 3.5 Hz, 1H); $^{13}$C NMR (CDCl$_3$, 400 MHz, ppm): δ 157.59, 154.82, 129.97, 122.24, 114.60, 74.34, 66.94, 66.44.

$^1$H NMR and $^{13}$C NMR spectra of compounds 1 through compound 8 are depicted in FIGS. 6-20 and FIG. 23.

Figure 22:
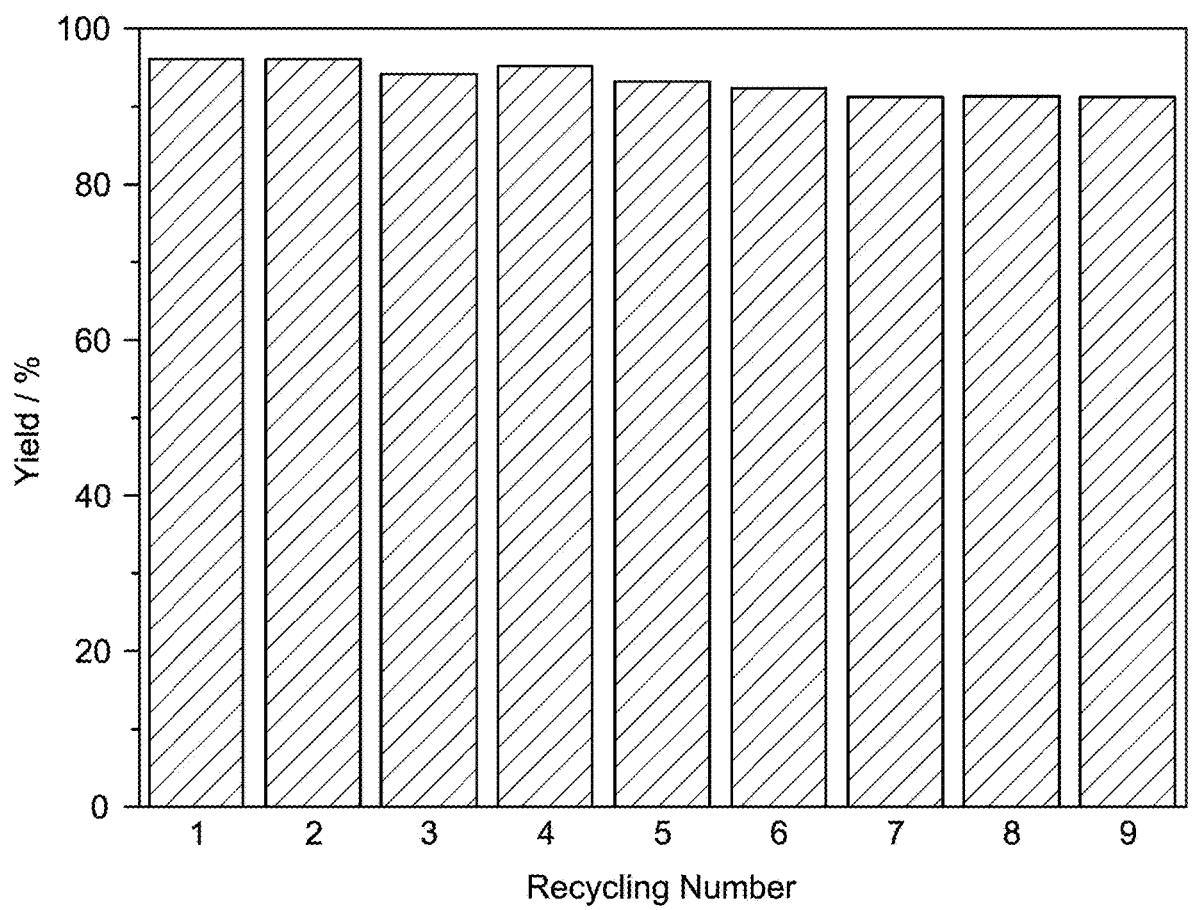
FIG. 22 is a graph depicting recycling tests with Pd-NP@COF-701 for the reaction of $CO_2$ with styrene oxide to form cyclic carbonates, according to certain embodiments.
Figure 23:
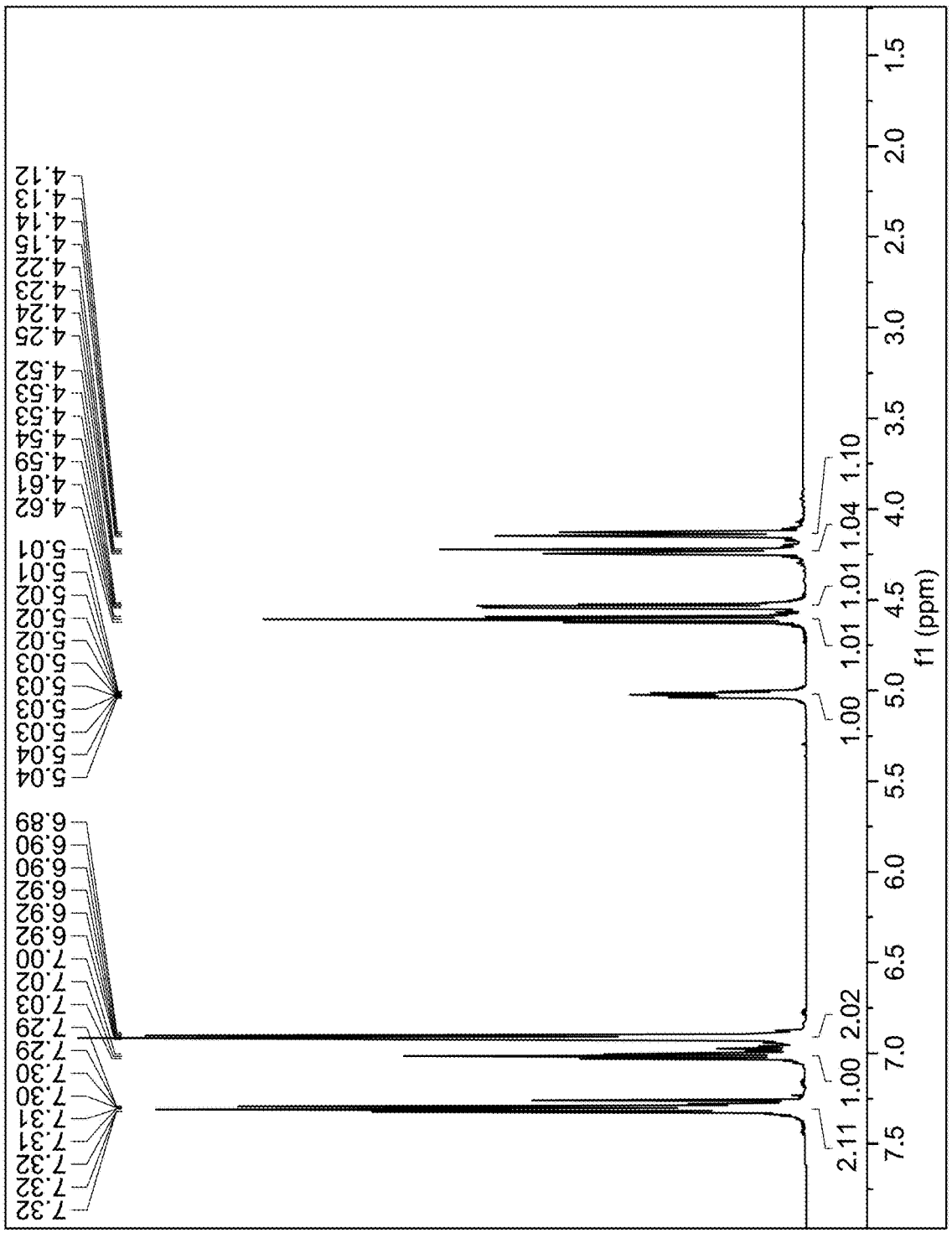
FIG. 23 is a $^{13}$C NMR spectrum of 4-(phenoxymethyl)-1,3-dioxolan-2-one (compound 8) recorded in $CDCl_3$ at 400 MHz, according to certain embodiments.

Recyclability of the Pd-NP@COF-701 catalyst was evaluated through repeated application in the cycloaddition of styrene oxide (SO) with carbon dioxide (CO$_2$) to form cyclic carbonates. As shown in FIG. 22, Pd-NP@COF-701 maintained high catalytic performance across nine consecutive reaction cycles, without observable degradation in catalytic efficiency or any adverse effects on the structural framework and connectivity of the catalyst.

Figure 21:
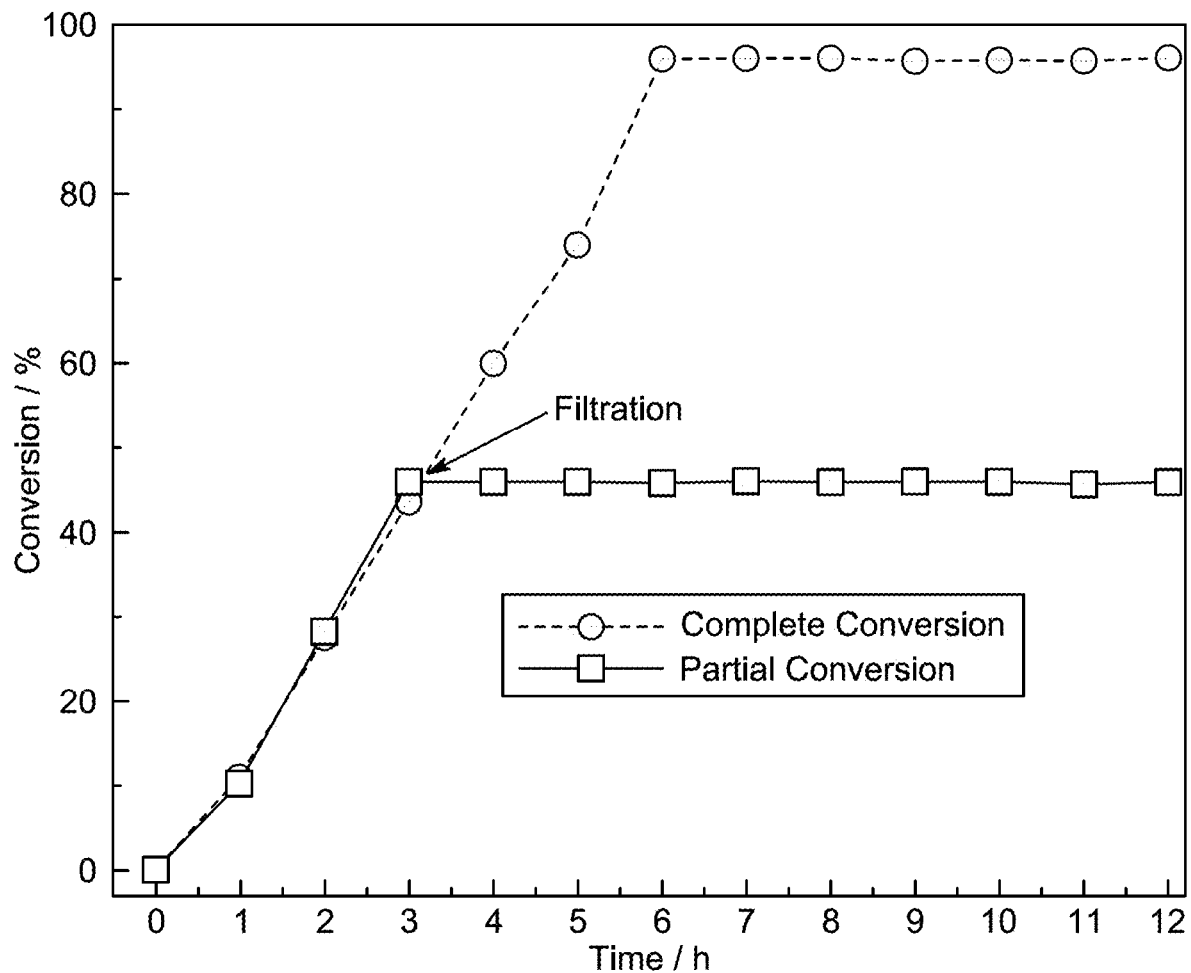
FIG. 21 is a leaching test of Pd-NP@COF-701 performed using a hot filtration method, according to certain embodiments.

To assess potential leaching of catalytically active species into the reaction medium, a leaching test was conducted using the hot filtration method. In this procedure, the catalyst was removed from the reaction mixture after two hours via filtration through a pre-heated frit, and the filtrate was subsequently monitored for continued catalytic activity. No further conversion of the reactants was observed, thereby confirming that catalytically active palladium species remained immobilized within the Pd-NP@COF-701 framework throughout the reaction. The results of this leaching test are presented in FIG. 21.

Figure 24:
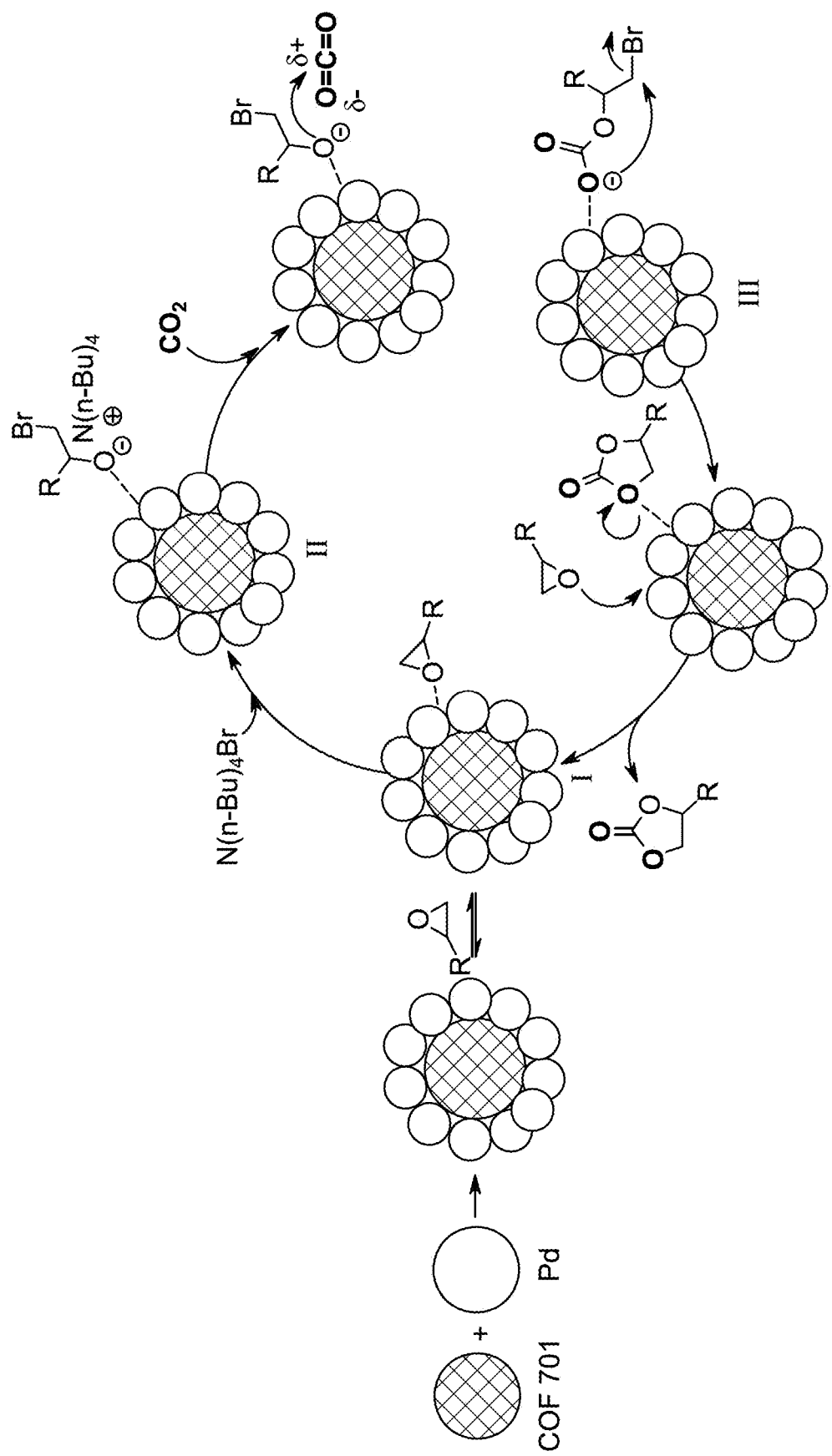
FIG. 24 is a schematic mechanism of forming cyclic carbonates from epoxides by Pd-NP@COF-701, according to certain embodiments.

From a mechanistic standpoint, the palladium nanoparticles embedded on the surface of COF-701 serve as Lewis acidic catalytic sites for the cycloaddition process. A mechanism for forming cyclic carbonates is depicted in FIG. 24. These Lewis acidic Pd centers form coordination complexes with the epoxide (i.e., SO) via its oxygen atom, resulting in the formation of intermediate adduct I. This intermediate subsequently undergoes a nucleophilic ring-opening attack by the bromide ion, generating a reactive intermediate II. Thereafter, carbon dioxide undergoes nucleophilic attack by the oxygen atom of the opened epoxide ring, leading to the formation of an alkyl carbonate anion III. Ring closure of this intermediate facilitates the formation of the cyclic carbonate product. Upon completion of the reaction, the cyclic carbonate dissociates from the Lewis acidic site, and the Pd-NP@COF-701 catalyst is regenerated and available for reuse in subsequent cycles.

Aspects of the present disclosure relate to a method of carbon dioxide fixation, comprising contacting a covalent organic framework material with a co-catalyst and an epoxide in the presence of carbon dioxide to form a cyclic carbonate. The covalent organic framework material includes reacted units of 2,4,6-trimethyl-1,3,5-triazine and reacted units 4,4'-biphenyldicarbaldehyde forming an olefin-linked framework structure, and palladium nanoparticles situated on the outer surface of the framework. The structural features of the framework, including olefinic linkages formed through aldol condensation and a nitrogen-rich core, were confirmed by spectroscopic and diffraction techniques. The presence of palladium nanoparticles on the surface of the framework, as observed by microscopy, and their distribution between the interlayer spaces, support coordination with the triazine units. The catalyst was applied to the cycloaddition of carbon dioxide and epoxides under a range of conditions, including in the presence of n-tetrabutylammonium bromide as a co-catalyst. High conversion and selectivity were achieved under moderate thermal and atmospheric pressure conditions. The catalyst exhibited performance across multiple cycles and was evaluated for a variety of aliphatic and aromatic epoxide substrates.

Numerous modifications and variations of the present disclosure are possible in light of the above teachings. It is therefore to be understood that within the scope of the appended claims, the disclosure may be practiced otherwise than as specifically described herein.

The invention claimed is:

1. A method of carbon dioxide fixation, comprising:
   contacting a covalent organic framework material with a co-catalyst and an epoxide in the presence of carbon dioxide to form a cyclic carbonate,
   recovering the covalent organic framework material after the contacting;
   washing the covalent organic framework material;
   drying the covalent organic framework material under vacuum at a temperature of 80 to 120° C. for 8 to 16 hours; and then
   contacting the covalent organic framework material with the co-catalyst and the epoxide in the presence of carbon dioxide to form the cyclic carbonate;
   wherein the covalent organic framework material comprises reacted units of a 2,4,6-trimethyl-1,3,5-triazine, reacted units of a 4,4'-biphenyldicarbaldehyde, and palladium nanoparticles,
   wherein the reacted units of the 2,4,6-trimethyl-1,3,5-triazine and the reacted units of the 4,4'-biphenyldicarbaldehyde form a COF-701,
   wherein the palladium nanoparticles are on an outer surface of the COF-701,
   wherein the co-catalyst is n-tetrabutylammonium bromide.

2. The method of claim 1, wherein the palladium nanoparticles have a diameter of 0.5 to 10 nm.

3. The method of claim 2, wherein the palladium nanoparticles have a diameter of 2 to 5 nm.

4. The method of claim 1, wherein the covalent organic framework material is in the shape of spheres having a diameter of 0.5 to 10 µm.

5. The method of claim 4, wherein the spheres are connected by a common facial aperture.

6. The method of claim 1, wherein the covalent organic framework material is porous, and the COF-701 has a pore width of 0.1 to 2 nm.

7. The method of claim 1, wherein the covalent organic framework material is at least 90 percent by weight (wt. %) stable at a temperature of 400° C. based on an initial weight of the covalent organic framework material.

8. The method of claim 1, wherein the epoxide is selected from the group consisting of 1,2-epoxypropane, 1,2-epoxybutane, 1,2-epoxyhexane, epichlorohydrin, allyl glycidyl ether, styrene oxide, and phenyl glycidyl ether.

9. The method of claim 8, wherein the epoxide is styrene oxide.

10. The method of claim 1, wherein the co-catalyst is an n-tetrabutylammonium salt.

11. The method of claim 1, wherein the contacting occurs at a temperature of 40 to 120° C.

12. The method of claim 1, wherein the contacting occurs at a temperature of 50 to 70° C.

13. The method of claim 1, wherein the contacting occurs for 4 to 14 hours.

14. The method of claim 1, wherein the carbon dioxide is at a pressure of 0.5 to 2 bar.

15. The method of claim 1, wherein a molar ratio of the co-catalyst to the epoxide is 5:1 to 1:5.

16. The method of claim 8, wherein at least 85% of the epoxide is converted to the cyclic carbonate based on a proton nuclear magnetic resonance spectrum.

17. The method of claim 9, wherein 95 to 97% of the epoxide is converted to the cyclic carbonate based on a proton nuclear magnetic resonance spectrum.

18. The method of claim 1, wherein a selectivity for the cyclic carbonate is at least 98% based on an integration of a —CH signal at 4.34 ppm in a proton nuclear magnetic resonance spectrum.

19. The method of claim 1, wherein after repeating the recovering, washing, drying, and contacting 8 to 10 times, the covalent organic framework material has a yield percentage of the cyclic carbonate of at least 90% of that of an initial yield percentage of the cyclic carbonate of the covalent organic framework material.

* * * * *